United States Patent
Seshimo et al.

(10) Patent No.: US 7,467,055 B2
(45) Date of Patent: Dec. 16, 2008

(54) METHOD FOR SETTING OPERATING CONDITION OF MEASURING APPARATUS, METHOD FOR MANAGING MEASUREMENT RESULT OF MEASURING APPARATUS, MEASURING SYSTEM, DATA PROCESSING APPARATUS FOR MEASURING APPARATUS, AND STORAGE MEDIUM

(75) Inventors: Hiroyuki Seshimo, Kobe (JP); Noriaki Koeda, Kobe (JP)

(73) Assignee: Sysmex Corporation, Kobe (JP)

( * ) Notice: Subject to any disclaimer, the term of this patent is extended or adjusted under 35 U.S.C. 154(b) by 302 days.

(21) Appl. No.: 11/298,185

(22) Filed: Dec. 9, 2005

(65) Prior Publication Data

US 2006/0140466 A1 Jun. 29, 2006

(30) Foreign Application Priority Data

Dec. 9, 2004 (JP) ............................. 2004-356135
Dec. 9, 2004 (JP) ............................. 2004-356141

(51) Int. Cl.
G01D 18/00 (2006.01)
G01D 1/00 (2006.01)
G01P 21/00 (2006.01)
G01R 35/00 (2006.01)

(52) U.S. Cl. ....................... 702/85; 702/127
(58) Field of Classification Search ............... 702/19, 702/22, 50, 80, 85
See application file for complete search history.

(56) References Cited

U.S. PATENT DOCUMENTS 6,711,448 B2* 3/2004 Misawa et al. ............. 700/83
7,085,661 B2* 8/2006 Emori et al. ................. 702/63
2004/0139270 A1* 7/2004 Masuda et al. ............... 711/1
2006/0069915 A1* 3/2006 Koeda ......................... 713/168

FOREIGN PATENT DOCUMENTS

JP H09-127121 A 5/1997
JP 2002-342111 * 11/2002

OTHER PUBLICATIONS

English Abstract of 2002-342111, Nov. 2002.*

* cited by examiner

*Primary Examiner*—Michael P Nghiem
(74) *Attorney, Agent, or Firm*—Brinks Hofer Gilson & Lione

(57) ABSTRACT

A data processing apparatus acquires, from a database, storage region designation data designating the storage region in which setting values of a measuring apparatus are stored and setting object designation data designating the setting object of the measuring apparatus, acquires setting values from a storage region of a first database specified by the acquired storage region designation data, and transmits the acquired setting object designation data and acquired setting values to the measuring apparatus. The data processing apparatus receives measurement result data from a measurement apparatus, acquires mutually associated object names and property names, and output table data and output field data from a database that mutually associates and stores object names and property names, and output table data and output field data, and stores the measurement result data specified by the acquired object name and property name in a storage region specified by the acquired output table data and output field data.

14 Claims, 19 Drawing Sheets

FIG.7

| ID | No. | Classification disp | Type display name | Setting name | Setting display name | Data | Data type | Min | Max | Combo list |
|---|---|---|---|---|---|---|---|---|---|---|
| ... | ... | ... | ... | ... | ... | ... | ... | ... | ... | ... |
| 24 | 2 | Measuring unit | Temperature check | TempCheck | Temperature check | 1 | Int | | | |
| 25 | 2 | Measuring unit | Air pressure source timer | PutimerEnable | Use | 2 | Sel | | | Use\|NO use |
| 26 | 2 | Measuring unit | Air pressure source timer | Putimer | Time out time | 3 | Int | 1 | 60 | |
| 27 | 2 | Measuring unit | Fluid unit | FlowUnit | Flow unit | 1 | Sel | 1 | | Standard\|organic medium unit |
| 28 | 2 | Measuring unit | Object lens unit | OLensUnit | Object lens unit | 2 | Sel | 2 | | 5x\|10x\|20x |
| 29 | 2 | Measuring unit | Dispersant unit | DispersantUnit | Dispersant unit | 1 | Sel | 1 | | Standard\|Ultrasound dispersion |
| 30 | 2 | Measuring unit | Gas sensor | GasSensor | Gas sensor | 1 | Long | | | |
| 31 | 2 | Measuring unit | Mix moter DA value | DCMTDA | Mix moter DA value | 353 | Long | | | |
| 32 | 2 | Measuring unit | Strobe DA value HPF | StrobeDAHPF | Strobe DA value HPF | 575 | Long | | | |
| 33 | 2 | Measuring unit | Strobe DA value LPF | StrobeDALPF | Strobe DA value LPF | 615 | Long | | | |
| 34 | 2 | Measuring unit | Ultrasound DA value | USDA | Ultrasound DA value | 20 | Long | | | |
| 35 | 2 | Measuring unit | Strobe brightness value HPF | LtHPF | Strobe brightness value HPF | 160 | Long | | | |
| 36 | 2 | Measuring unit | Strobe brightness value LPF | LtLPF | Strobe brightness value LPF | 160 | Long | | | |
| 37 | 2 | Measuring unit | Target temperature | TempTarget | Target temperature | 250 | Int | | | |
| 38 | 2 | Measuring unit | Temperature adjustment | TempAdjust | Temperature adjustment | 1 | Sel | | | YES\|NO |
| 39 | 2 | Measuring unit | Maximum repeats | MaxMeasCount | Maximum repeats | 99 | Int | | 999 | |
| ... | ... | ... | ... | ... | ... | ... | ... | ... | ... | ... |

| Setting name | Setting value |
|---|---|
| SOP ID | 1 |
| BGCorrection | 1 |
| ⋮ | ⋮ |
| BinMethod | 1 |
| SmothingFilter | 1 |
| EnhancingFilter | 1 |
| BinThreshA | 0.5 |
| BinThreshB | 0.7 |
| ParticleAdjust | 2 |
| DilRate | 1 |
| Smothing | 2 |
| Gakubuchihosei | 2 |
| FlagDns | 2 |
| DType | PRMDT1 |
| DLog | 1 |
| DPartition | 226 |
| DUpperLimit | 10000 |
| DLowerLimit | 0.3 |
| DUpperPercent | 100 |
| DLowerPercent | 1 |
| DAxisMax | 10000 |
| DAxisMin | 0.3 |
| CType | PRMDT4 |
| CLog | 2 |
| CPartition | 80 |
| CUpperLimit | 1 |
| CLowerLimit | 0 |
| CUpperPercent | 90 |
| CLowerPercent | 10 |
| CAxisMax | 1 |
| CAxisMin | 0.2 |
| MeasMode | 1 |
| TmPeakCount | 1 |
| MaxMeasCount | 1 |
| MaxCount | 1 |
| TargetValve | 0.5 |
| SySpeedL | 100 |
| SySpeedH | 30 |
| ⋮ | ⋮ |

DB2

36a — Setting name
36b — Setting value

FIG.9

| ID | Table name | Setting name | Setting display name | Data type | Default value | Combo list | Max value | Min value | | | | | | |
|---|---|---|---|---|---|---|---|---|---|---|---|---|---|---|
| ... | ... | ... | ... | ... | ... | | | ... | ... | ... | ... | ... | ... | ... |
| 4 | ANADT | BGCorrection | BG correction | Sel | 1 | YES\|NO | | | | | | | | |
| 5 | ANADT | BinMethod | Binarization method | Sel | 1 | Standard\|Other | | | | | | | | |
| 6 | ANADT | SmoothingFilter | Smoothing filter | Sel | 2 | Median\|Other | | | | | | | | |
| 7 | ANADT | EnhancingFilter | Edge enhancement level | Sel | 2 | 2D filter\|Other | | | | | | | | |
| 8 | ANADT | BinThreshA | Binarization Threshold value A | float | | | | | | | | | | |
| 9 | ANADT | BinThreshB | Binarization Threshold value B | float | | | | | | | | | | |
| 10 | ANADT | ParticleAdjust | Particle size adjustment | Sel | 2 | YES\|NO | | | | | | | | |
| 11 | ANADT | DilRate | Dilution rate | float | 1 | | | | | | | | | |
| 12 | ANADT | Smoothing | Smoothing | Sel | 2 | YES\|NO | | | | | | | | |
| 13 | ANADT | Gakubuchihosei | Frame correction | Sel | 2 | YES\|NO | | | | | | | | |
| 14 | ANADT | FlagDns | Density correction | Sel | 2 | YES\|NO | | | | | | | | |
| 15 | ANADT | DType | Particle size type | Custom | PRMDT1 | | | | | | | | | |
| 16 | ANADT | DLog | Particle axis attribute (Log/linear) | Sel | 1 | Linear display\|Log display | | | | | | | | |
| 17 | ANADT | DPartition | Particle partition width | long | 226 | | 512 | 1 | | | | | | |
| 18 | ANADT | DUpperLimit | Particle size upper value | float | | | 40000 | 0.3 | | | | | | |
| 19 | ANADT | DLowerLimit | Particle size lower value | float | | | 40000 | 0.3 | | | | | | |
| 20 | ANADT | DUpperPercent | Particle size upper % | float | | | 100 | 51 | | | | | | |
| 21 | ANADT | DLowerPercent | Particle size lower % | float | | | 50 | 1 | | | | | | |
| 22 | ANADT | DAxisMax | Particle axis max value | float | | | 40000 | 0.3 | | | | | | |
| 23 | ANADT | DAxisMin | Particle axis min value | float | | | 40000 | 0.3 | | | | | | |
| 24 | ANADT | CType | Shape type | Custom | PRDT4 | | | | | | | | | |
| 25 | ANADT | CLog | Shape axis attributes (log/linear) | Sel | 2 | Linear display\|Log display | | | | | | | | |
| 26 | ANADT | CPartition | Shape partition width | long | 80 | | 512 | 1 | | | | | | |
| 27 | ANADT | CUpperLimit | Shape upper value | float | | | 1 | 0 | | | | | | |
| 28 | ANADT | CLowerLimit | Shape lower value | float | | | 1 | 0 | | | | | | |
| 29 | ANADT | CUpperPercent | Shape upper % | float | 90 | | 100 | 51 | | | | | | |
| 30 | ANADT | CLowerPercent | Shape lower % | float | 10 | | 50 | 1 | | | | | | |
| 31 | ANADT | CAxisMax | Shape axis max value | float | 1 | | 1 | 0 | | | | | | |
| 32 | ANADT | CAxisMin | Shape axis min value | float | 0.2 | | 1 | 0 | | | | | | |
| 33 | MRESULT | MeasMode | Measuring mode | Sel | 1 | HPF\|LPF\|LPF->HPF | | | | | | | | |
| 34 | MRESULT | TmPeakCount | Time count/total count | long | 1 | Time count\|Total count | | | | | | | | |
| 35 | MRESULT | MaxCount | Max count no. | long | 1 | | | | | | | | | |
| 36 | MRESULT | MaxMeasCount | No. repeats | long | 1 | | 9999 | 1 | | | | | | |
| 37 | MRESULT | TargetValve | Target pressure | float | | | | | | | | | | |
| 38 | MRESULT | SySpeedL | Syringe speed LPF | long | | | 1000 | 10 | | | | | | |
| ... | ... | ... | ... | ... | ... | ... | ... | ... | | | | | | |

| ID | Item display name | Input table | Input item | Object | Property | Flag 1 | Flag 2 | Flag 3 | ... |
|---|---|---|---|---|---|---|---|---|---|
| ... | ... | ... | ... | ... | ... | ... | ... | ... | ... |
| 3 | Measure mode | SOPCODEDEF | MeasMode | MeasSettings | MeasMode | 1 | 1 | 1 | ... |
| ... | ... | ... | ... | ... | ... | ... | ... | ... | ... |
| 6 | Count method | SOPCODEDEF | TmPeakCount | MeasSettings | TmPeakCount | 1 | 1 | 1 | ... |
| 7 | Total repeats | SOPCODEDEF | MaxMeasCount | MeasSettings | MaxMeasCount | 1 | 1 | 1 | ... |
| 8 | Max count no. | SOPCODEDEF | MaxCount | MeasSettings | MaxCount | 1 | 1 | 1 | ... |
| 9 | Sheath fluid in use | SOPCODEDEF | Dispersant | MeasSettings | Dispersant | 1 | 1 | 1 | ... |
| 10 | Sheath fluid ID | SOPCODEDEF | DispensID | MeasSettings |  | 0 | 0 | 0 | ... |
| 11 | Target pressure | DISPENSM | RinsePress | MeasSettings | TargetValue | 1 | 1 | 1 | ... |
| 12 | Syringe speed LPF | DISPENSM | SampleSilingeSpeed | MeasSettings | SySpeedL | 1 | 1 | 1 | ... |
| 13 | Syringe speed HPF | SOPCODEDEF | SySpeedH | MeasSettings | SySpeedH | 1 | 1 | 1 | ... |
| 14 | Sheath speed (L) | SOPCODEDEF | SeathSpeedL | MeasSettings | SeathSpeedL | 1 | 1 | 1 | ... |
| 15 | Sheath speed (H) | DISPENSM | SeathSilingeSpeed | MeasSettings | SeathSpeedH | 1 | 1 | 1 | ... |
| ... | ... | ... | ... | ... | ... | ... | ... | ... | ... |
| 57 | Detection unit target temp | SYSTEMM | TempTarget | MeasSettings | TempTarget | 1 | 1 | 1 | ... |
| 58 | Room temp adjustment | SYSTEMM | TempAdjust | MeasSettings | TempAdjust | 1 | 1 | 1 | ... |
| 59 | Object lens unit | SYSTEMM | OLensUnit | MeasSettings | OLensUnit | 1 | 1 | 1 | ... |
| ... | ... | ... | ... | ... | ... | ... | ... | ... | ... |

| ID | Item display name | Output table | Output field | Object | Property | ... |
|---|---|---|---|---|---|---|
| ⋮ | ⋮ | ⋮ | ⋮ | ⋮ | ⋮ | ... |
| 3 | Measure mode | MRESULT | MeasMode | MeasSettings | MeasMode | ... |
| ⋮ | ⋮ | ⋮ | ⋮ | ⋮ | ⋮ | ... |
| 6 | Count method | MRESULT | MetaData | MeasSettings | TmPeakCount | ... |
| 7 | Total repeats | MRESULT | MetaData | MeasSettings | MaxMeasCount | ... |
| 8 | Max count no. | MRESULT | MetaData | MeasSettings | MaxCount | ... |
| 9 | Sheath fluid in use | MRESULT | MetaData | MeasSettings | Dispersant | ... |
| 10 | Sheath fluid ID | MRESULT | MetaData | MeasSettings | DispersID | ... |
| 11 | Target pressure | MRESULT | MetaData | MeasSettings | TargetValue | ... |
| 12 | Syringe speed LPF | MRESULT | MetaData | MeasSettings | SySpeedL | ... |
| 13 | Syringe speed HPF | MRESULT | MetaData | MeasSettings | SySpeedH | ... |
| 14 | Sheath speed (L) | MRESULT | MetaData | MeasSettings | SeathSpeedL | ... |
| 15 | Sheath speed (H) | MRESULT | MetaData | MeasSettings | SeathSpeedH | ... |
| ⋮ | ⋮ | ⋮ | ⋮ | ⋮ | ⋮ | ... |
| 57 | Detection unit target temp | MRESULT | MetaData | MeasSettings | TempTarget | ... |
| 58 | Room temp compensation | MRESULT | MetaData | MeasSettings | TempAdjust | ... |
| 59 | Object lens unit | MRESULT | MetaData | MeasSettings | OLensUnit | ... |
| ⋮ | ⋮ | ⋮ | ⋮ | ⋮ | ⋮ | ... |
| 177 | Particle density | ANARESULT | Density | LimResult | Density | ... |
| 178 | Small particle ratio | ANARESULT | DSSizeRatio | LimResult | DSSizeRatio | ... |
| 179 | Mid particle ratio | ANARESULT | DMSizeRatio | LimResult | DMSizeRatio | ... |
| 180 | Large particle ratio | ANARESULT | DLSizeRatio | LimResult | DLSizeRatio | ... |
| 181 | Particle limit ratio | ANARESULT | DLimRatio | LimResult | DLimRatio | ... |
| 182 | Detected particle no. | ANARESULT | TotalCount | LimResult | TotalCount | ... |
| 183 | Valid analysis no. | ANARESULT | ValidCount | LimResult | ValidCount | ... |
| 184 | Limit particle no. | ANARESULT | LimCount | LimResult | LimCount | ... |
| ⋮ | ⋮ | ⋮ | ⋮ | ⋮ | ⋮ | ... |

Columns: 39a, 39b, 39c, 39d, 39e, 39f

Device settings

| Type | Type name | Item | Value |
|---|---|---|---|
| system | ID no. | serial no. | 123-4567-1 |
| | | Device ID | FPIA-1 |
| | | Device type | FPIA-3000 |
| | remote control | remote control | No |
| | print | auto print | No |
| | record operation | auto erase | Yes |
| | | validation function | Yes |
| | | auto validation | Yes |
| | quality control | scheduled start | No |
| measuring unit | Blank check | HPF Blank upper lim | 45 |
| | | HPF Blank upper lim | 45 |
| | Air pressure source timer | enable | Yes |
| | | time out | 10 |
| | Temp | sheath temp (lower | 35 |
| | | sheath temp (upper | 45 |
| | | flow cell (lower limit) | 35 |
| | | flow cell (upper limit) | 45 |
| | | object lens (lower li | 35 |
| | | object lens (upper li | 45 |
| | | outside air temp (lo | 10 |
| | | outside air temp (up | 35 |
| Transmission | General | auto send (serial) | No |
| | | auto send (LAN) | No |
| | | size table send | No |
| | | shape table send | No |
| | | scattergram send | No |

Print  Export  OK  Cancel

METHOD FOR SETTING OPERATING CONDITION OF MEASURING APPARATUS, METHOD FOR MANAGING MEASUREMENT RESULT OF MEASURING APPARATUS, MEASURING SYSTEM, DATA PROCESSING APPARATUS FOR MEASURING APPARATUS, AND STORAGE MEDIUM

This application claims priority under 35 U.S.C. § 119 to Japanese Patent Application No. 2004-356135 and 2004-356141 both filed Dec. 9, 2004, the entire content of which is hereby incorporated by reference.

FIELD OF THE INVENTION

The present invention relates to a method for setting operating condition of a measuring apparatus, a method for managing measurement result of a measuring apparatus, a measuring system using the measuring apparatus, data processing apparatus for a measuring apparatus, and a computer readable storage medium for recording computer programs that enable a computer to function as the data processing apparatus for a measuring apparatus.

BACKGROUND

Measuring apparatuses (blood analyzers, urine analyzers, stool analyzers, particle analyzers and the like) for measuring various profiles of specimens (blood specimens, urine specimens, stool specimens, or particle specimens and the like) are well known. These measuring apparatuses are using in measuring systems in which the measuring apparatuses are connected through an electrical communication line to data processing apparatuses configured by a computer provided with installed computer programs that are used to perform necessary processing of measurement data, and management of measurement results and analysis results, such that the processing of measurement data, and display and management of measurement results can be performed by the data processing apparatus. Such data processing apparatuses have a function for setting the measurement conditions of the measuring apparatus (for example, refer to Japanese Laid-Open Patent Publication No. 9-127121).

In typical data processing apparatuses, a range of set values or values for the setting values for each setting object of the measuring apparatus are predefined, so the user can select a setting value within a defined range for each setting object. The setting values selected by the user in this manner are transmitted from the data processing apparatus to the measuring apparatus to set the measuring conditions of the measuring apparatus. This type of data processing apparatus receives measurement values and setting values of the measurement conditions during measurement from the measuring apparatus after the measurements are completed. These measurement values and setting values correspond individually to measurement items and setting items, and the data processing apparatus specifies the received measurement value and setting values, stores the measurement values and setting values in a database that allocates areas for each item (measurement items and setting items), and manages the measurement result data (in this case, measurement values and setting values).

In the previously described conventional data processing apparatus, however, problems have arisen inasmuch as the components of the computer programs for a function for setting the measurement conditions of the measuring apparatus and a function for managing the measurement results of the measuring apparatus are specially designed for each model of measuring apparatus, as well as managing these data, such that the design and number of development stages are increased for the reasons described in sections (1) and (2) below.

(1) The storage region (database fields) designation data designating the storage regions for storing the measurement data, setting object designation data designating the setting object, the measurement result designation data designating measurement result data, and the setting value are incorporated in the program code of the previously mentioned computer program.

(2) Since the structure of the aforesaid measuring apparatus will differ according to the type (model), the setting objects of the measuring apparatus, setting values used to set the setting objects, and measurement items and setting items of the measuring apparatus must be individually defined for each type of measuring apparatus.

Furthermore, In the previously mentioned conventional data processing apparatus, the program code must be modified and the computer program recompiled when the specifications of the measuring apparatus are changed, and when new setting objects, setting values, measurement items, or setting items are defined, thus requiring very complex labor.

SUMMARY OF THE INVENTION

The scope of the present invention is defined solely by the appended claims, and is not affected to any degree by the statements within this summary.

The first aspect of the present invention relates to a method for setting operating condition of a measuring apparatus comprising the steps of: acquiring mutually associated storage region specification data and setting object specification data from a database storing mutually associated the storage region specification data and the setting object specification data, the storage region specification data specifying the storage region for storing setting values used in setting the measuring apparatus, and the setting object specification data specifying a setting object of the measuring apparatus; acquiring setting values from the storage region specified by the acquired storage region specification data; and setting the setting object specified by the acquired setting object specification data by the acquired setting value.

The second aspect of the present invention relates to a method for managing measurement result of a measuring apparatus comprising the steps of: acquiring measurement result data from the measuring apparatus; acquiring mutually associated measurement result specification data and storage region specification data from a database storing the mutually associated measurement result specification data and storage region specification data, the measurement result specification data specifying measurement result data, and the storage region specification data specifying the storage region for storing the measurement result data; and storing the measurement result data specified by the acquired measurement result specification data in a storage region specified by the acquired storage region specification data.

The third aspect of the present invention relates to a measuring system comprising: a measuring apparatus provided with a plurality of setting objects; a first database for storing setting values used in setting the measuring apparatus; a second database for mutually associating and storing storage region designation data and setting object designation data, the storage region designation data designating a storage region at which the setting value is stored in the first database, and the setting object designation data designating the setting objects of the measuring apparatus; a first acquiring means for acquiring the mutually associated storage region designation data and setting object designation data from the second database; a second acquiring means for acquiring the setting value from the storage region of the first database specified by the storage region designation data acquired by the first acquiring means; and a setting means for setting the setting object specified by the setting object designation data acquired by the first acquiring means by the setting value acquired by the second acquiring means.

The fourth aspect of the present invention relates to a measuring system comprising: a measuring apparatus for measuring a measurement object and outputting measurement result data; a database for storing mutually associated measurement result designation data and storage region designation data, the measurement result designation data designating the measurement result data, and the storage region designation data designating a storage region at which the measurement result data are stored; a first acquiring means for acquiring the measurement result data from the measuring apparatus; a second acquiring means for acquiring the mutually associated measurement result designation data and storage region designation data from the database; and a storage means for storing the measurement result data specified by the measurement result designation data acquired by the second acquiring means in the storage region specified by the storage region designation data acquired by the second acquiring means.

The fifth aspect of the present invention relates to a data processing apparatus for a measuring apparatus capable of communicating with a measuring apparatus having a plurality of setting objects comprising: a first database for storing setting values used for setting the measuring apparatus; a second database for mutually associating and storing storage region designation data and setting object designation data, the storage region designation data designating a storage region at which the setting value is stored in the first database, and the setting object designation data designating the setting objects of the measuring apparatus; a first acquiring means for acquiring the mutually associated storage region designation data and setting object designation data from the second database; a second acquiring means for acquiring the setting value from the storage region of the first database specified by the storage region designation data acquired by the first acquiring means; and a transmitting means for transmitting the setting object designation data acquired by the first acquiring means, and the setting value acquired by the second acquiring means to the measuring apparatus.

The sixth aspect of the present invention relates to a data processing apparatus for a measuring apparatus capable of communicating with a measuring device that outputs measurement results comprising: a database for storing mutually associated measurement result designation data and storage region designation data, the measurement result designation data designating the measurement result data, and the storage region designation data designating a storage region at which the measurement result data are stored; a receiving means for receiving the measurement result data from the measuring apparatus; an acquiring means for acquiring the mutually associated measurement result designation data and storage region designation data from the database; and a storage means for storing the measurement result data specified by the measurement result designation data acquired by the acquiring means in the storage region specified by the storage region designation data acquired by the acquiring means.

The seventh aspect of the present invention relates to a computer readable storage medium storing a computer program that causes a computer which executes the computer program to function as: a first acquiring means for acquiring storage region specification data and setting object specification data from a second database, wherein a first database stores setting values used for setting of operating condition of a measuring apparatus, and the second database stores storage region specification data specifying the storage region storing the setting value in the first database and setting object specification data specifying the setting objects of the measuring apparatus; a second acquiring means for acquiring a setting value from the storage region of the first database specified by the storage region specification data acquired by the first acquiring means; and a transmitting means for transmitting to the measuring apparatus the setting object specification data acquired by the first acquiring means and the setting values acquired by the second acquiring means.

The eighth aspect of the present invention relates to a computer readable storage medium storing a computer program that causes a computer which executes the computer program to function as: a receiving means for receiving a measurement result data from a measuring apparatus, wherein measurement result specification data and storage region specification data are stored in a database and mutually associated, the measurement result specification data specifying the measurement result data, and the storage region specification data specifying a storage region at which the measurement result data are stored; an acquiring means for acquiring the mutually associated measurement result specification data and storage region specification data from the database; and a storage means for storing the measurement result data specified by the measurement result specification data acquired by the acquiring means in the storage region specified by the storage region specification data acquired by the acquiring means.

BRIEF DESCRIPTION OF THE DRAWINGS

FIG. 7 is a schematic view showing the structure of a database DB1 of an embodiment of the present invention;

FIG. 8 is a schematic view showing the structure of a database DB2 of an embodiment of the present invention;

FIG. 9 is a schematic view showing the structure of a database DB3 of an embodiment of the present invention;

FIG. 10 is a schematic view showing the structure of a database DB4 of an embodiment of the present invention;

FIG. 11 is a schematic view showing the structure of a database DB5 of an embodiment of the present invention;

FIG. 14 is a schematic view showing a window for setting measurement and analysis conditions in the application program of an embodiment of the present invention;

FIG. 16 is a schematic view of a window for basic settings of the particle analyzer in an application program of an embodiment of the present invention;

DESCRIPTION OF THE PREFERRED EMBODIMENTS

The embodiments of the present invention are described hereinafter based on the drawings.

Figure 1:
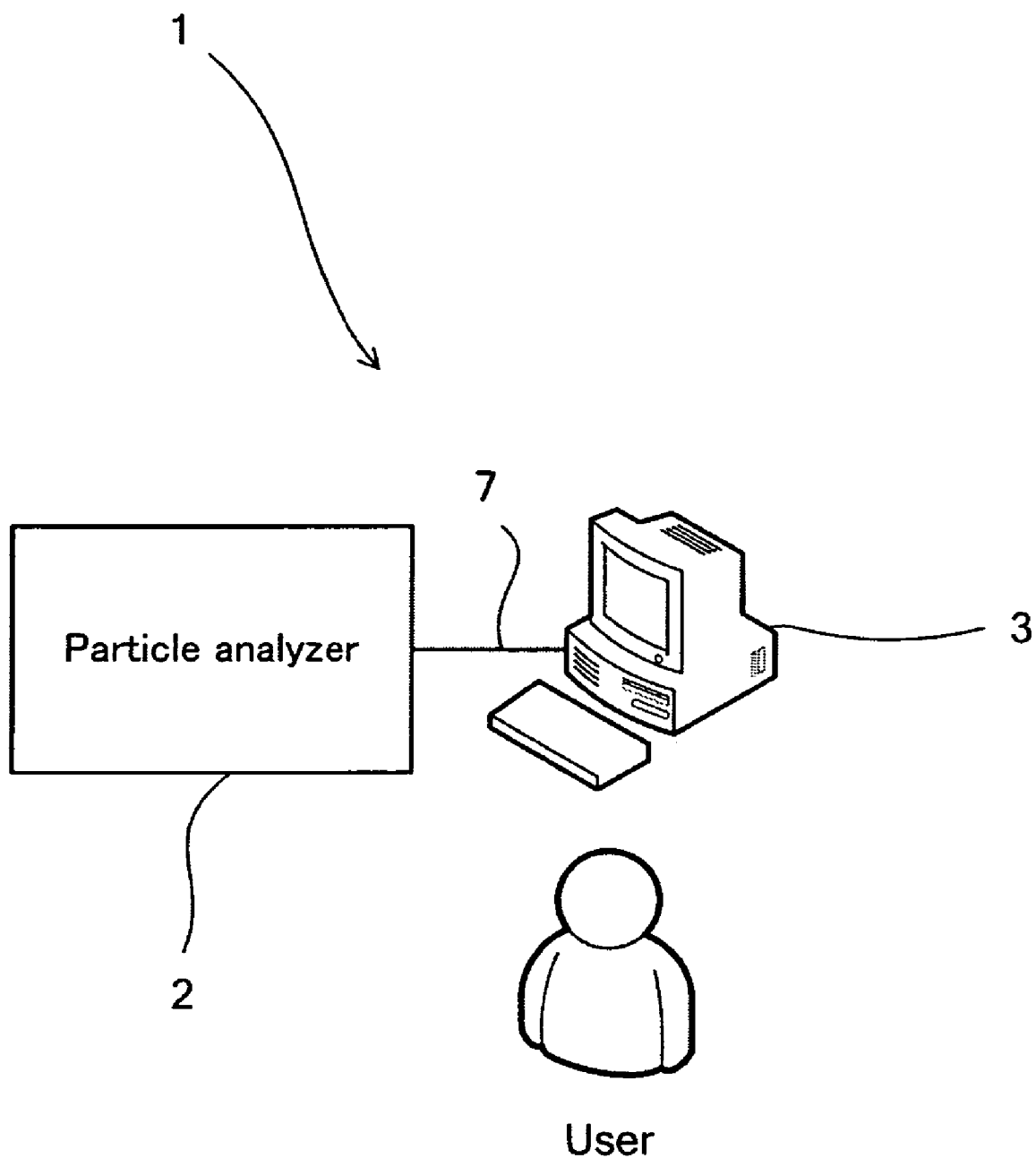
FIG. 1 is a schematic view showing the structure of an embodiment of the measuring system of the present invention.

FIG. 1 is a schematic view showing the structure of an embodiment of the measuring system of the present invention. As shown in FIG. 1, the measuring system 1 of the embodiment of the present invention mainly includes a particle analyzer 2 and data processing apparatus 3. The measuring system 1 is installed within a facility, such as a commercial facility that generally measures particles, research facility, hospital, or pathology research facility or the like. The particle analyzer 2 and data processing apparatus 3 are connected by an electrical signal cable 7 so as to be mutually capable of data communication.

Figure 2:
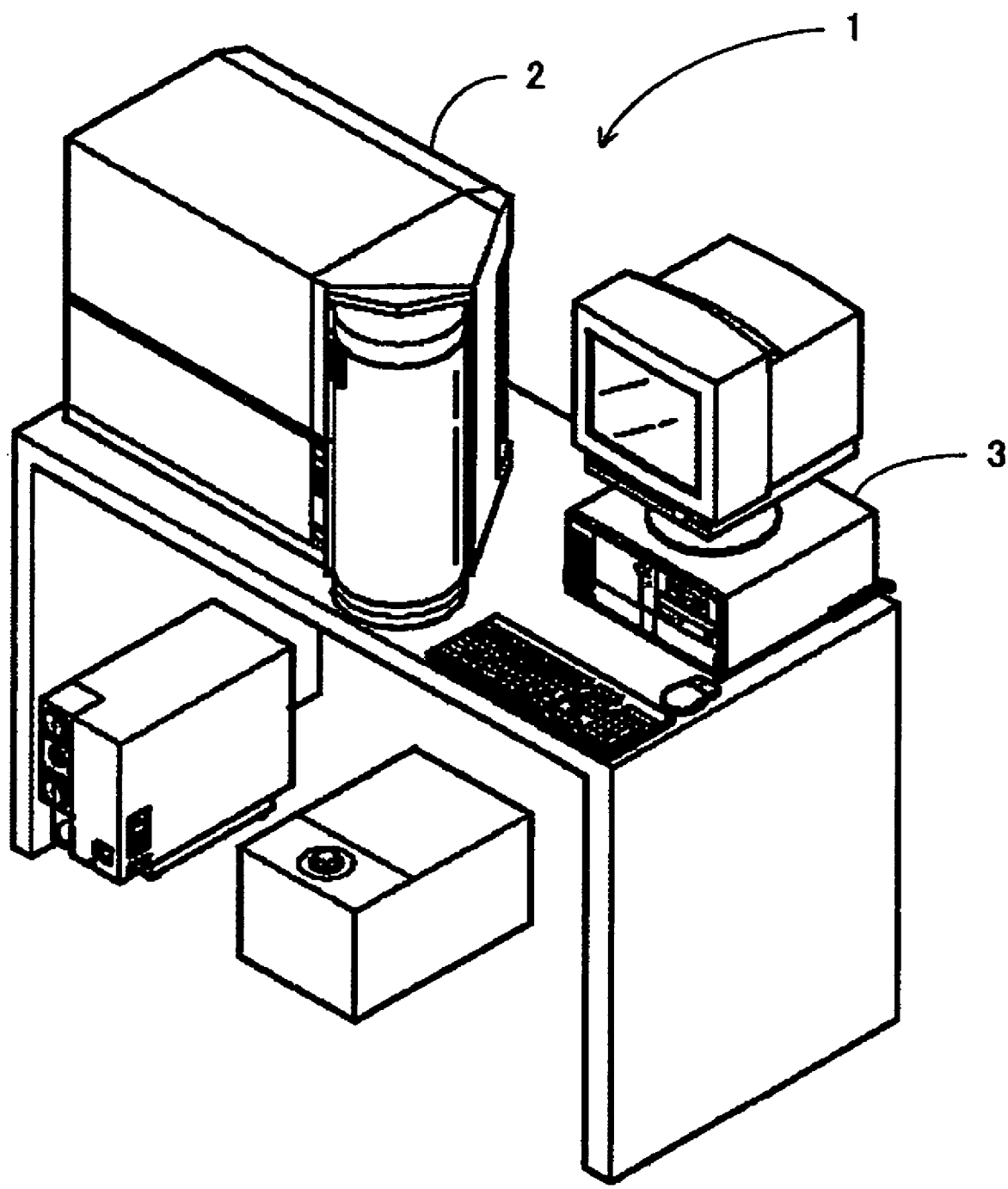
FIG. 2 is a perspective view showing the structure of an embodiment of the measuring system of the present invention.

FIG. 2 is a perspective view showing the structure of an embodiment of the measuring system of the present invention. The particle analyzer 2 of the present embodiment is configured so as to acquire a particle image, generate a partial image that includes the image of a particle from the particle image, and transmit the partial image to the data processing apparatus 3. An application program 34a, described later, is installed in the data processing apparatus 3, such that various processes, such as image processing and analysis processing of the received partial image, and a setting process for setting the measurement conditions of the particle analyzer 2 are executed by the application program 34a.

Figure 3:
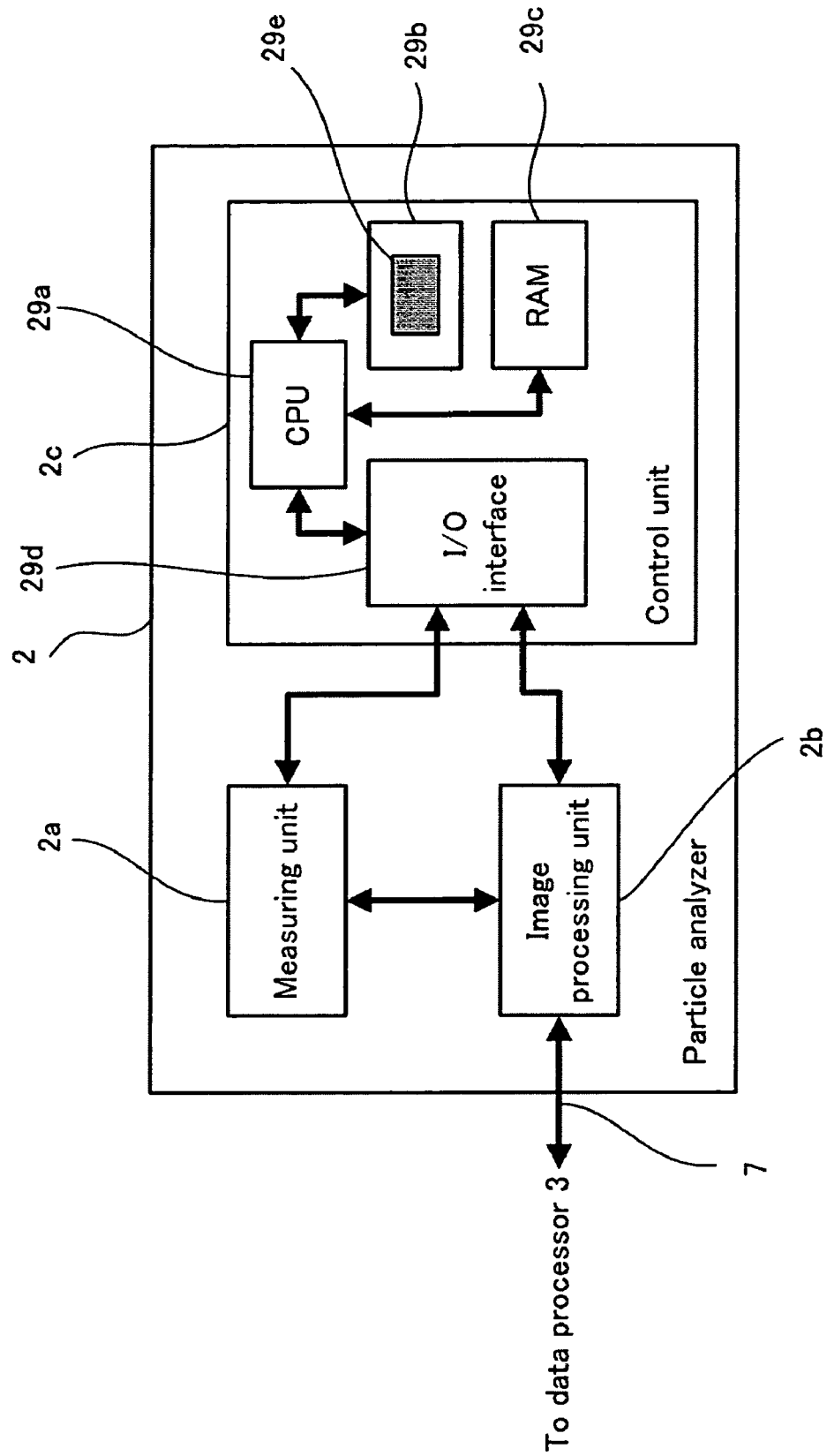
FIG. 3 is a block diagram showing the structure of a particle analyzer of an embodiment of the present invention.

FIG. 3 is a block diagram showing the structure of a particle analyzer of an embodiment of the present invention. As shown in FIG. 3, the particle analyzer 2 mainly includes a measuring unit 2a, image processing unit 2b, and control unit 2c.

Figure 4:
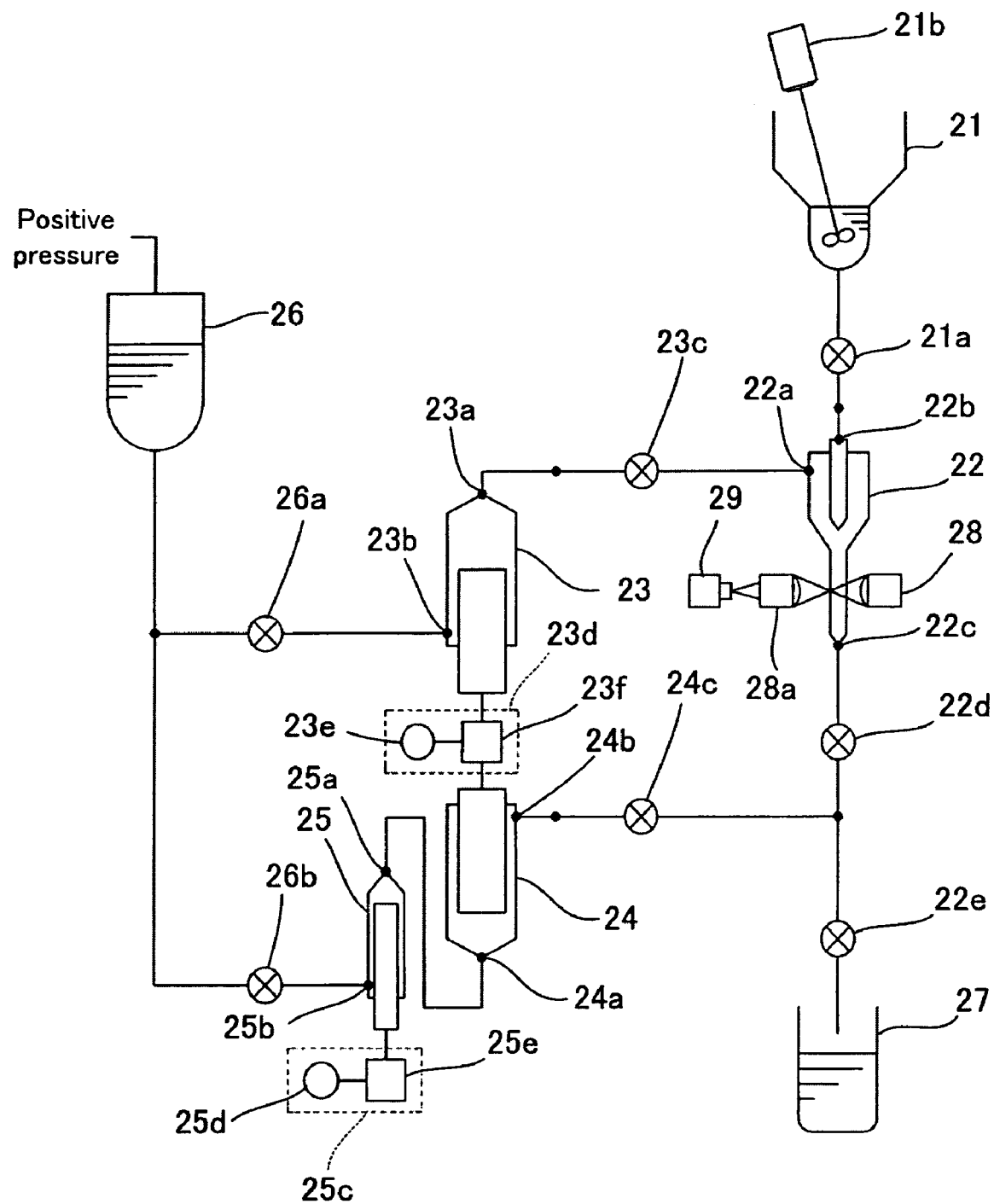
FIG. 4 is a schematic view showing the structure of the measuring unit provided in the particle analyzer of an embodiment of the present invention.

As shown in FIG. 4, the measuring unit 2a, mainly includes a sample container 21, sheath flow cell 22, syringe pumps 23, 24, 25, sheath fluid container 26, waste container 27, strobe lamp 28, and video camera 29; a particle suspension from the sample container 21 is supplied to the sheath flow cell 22, and sheath fluid is supplied to the sheath flow cell 22 so as to encapsulate the particle suspension and form a flat particle suspension flow, and the particles contained in the particle suspension are then photographed by the video camera 29.

The structure of the measuring unit 2a is described in detail below. As shown in FIG. 3, the sheath flow cell 22 has a sheath fluid supply inlet 22a, sample fluid supply inlet 22b, and waste outlet 22c for discharging the sheath fluid and sample fluid mixture. The sample container 21 is open at the top so as to be capable of holding sample fluid in the interior, and a discharge outlet is provided at the bottom. The discharge outlet of the sample container 21 is connected to the sample fluid supply inlet 22b through a flow path. An electromagnetic valve (hereinafter referred to as "valve") 21a is provided in the flow path between the discharge outlet of the sample container 21 and the sample fluid supply inlet 22b. Furthermore, a mixing device 21b is provided to mix the sample fluid within the sample container 21. The sample fluid is a particle suspension fluid containing particles.

The syringe pump 23 has a discharge port 23a and sheath fluid supply port 23b. The discharge port 23a is connected to the sheath fluid supply inlet 22a of the sheath flow cell 22. A valve 23c is provided in the flow path between the discharge port 23a and the sheath fluid supply inlet 22a. The sheath fluid container 26 is capable of accommodating sheath fluid, and a discharge outlet is provided at the bottom. The discharge outlet of the sheath fluid container 26 is connected to the sheath fluid supply port 23b through a flow path. A valve 26a is provided in the flow path between the discharge outlet of the sheath fluid container 26 and the sheath fluid supply port 23b.

The syringe pump 24 has two discharge ports 24a and suction ports 24b, and the syringe pump 25 has two suction ports 25a and sheath fluid supply ports 25b. The discharge port 24a of the syringe pump 24 is connected to the suction port 25a of the syringe pump 25 through a flow path.

The discharge outlet 22c of the sheath flow cell 22 is connected to the suction port 24b of the syringe pump 25 through a flow path, and the flow path branches midway with the end of a branch connected to the open top of the waste container 27. A valve 22d is provided in the flow path between the discharge outlet 22c and the branch point, and a valve 24c is provided in the flow path between the branch point and the suction port 24b. Furthermore, a valve 22e is provided in the flow path between the branch point and the opening of the waste container 27.

The sheath fluid supply port 25b of the syringe pump 25 is connected to the outlet of the sheath fluid container 26 through a flow path. A valve 26b is provided in the flow path between the discharge outlet of the sheath fluid container 26 and the sheath fluid supply port 25b.

The syringe pumps 23 and 24 are actuated in linkage with a single first drive source 23d, and the syringe pump 25 is actuated by a second drive source 25c. The first drive source 23d is provided with a stepping motor 23e, and transmission mechanism 23f for converting the rotational movement of the stepping motor 23e to linear movement, and transmitting the linear movement to the syringe pumps 23 and 24. The transmission mechanism 23f is configured by a drive pulley provided on the drive shaft of the stepping motor 23e, and a driven pulley, with a timing belt reeved therebetween, such that the rotational movement of the stepping motor 23e is converted to linear movement.

The second drive source 25c is provided with a stepping motor 25d, and a transmission mechanism 25e for converting the rotational movement of the stepping motor 25d to linear movement, and transmitting the linear movement to the syringe pump 25. The transmission mechanism 25e is configured by a drive pulley provided on the drive shaft of the stepping motor 25d, and a driven pulley, with a timing belt reeved therebetween, such that the rotational movement of the stepping motor 25d is converted to linear movement. The mixing device 21b is inserted into the sample fluid container 21 from the open top, so as to mix the sample fluid accommodated in the container 21.

The sheath flow cell 22 is provided with a strobe lamp 28 for illuminating the sample fluid that is narrowly constricted and encapsulated in the sheath fluid, and an object lens 28a, relay lens 28b, and video camera 29 for photographing the particles within the sample fluid flow. The object lens 28a is provided at three levels of magnification, 5×, 10×, and 20×, so as to be selectively settable for photographic use from among the three objective lenses 28a. Furthermore, the relay lens 28b is provided at two levels of magnification, 2× and 0.5×, so as to be selectively settable for photographic use from among the two relay lenses 28b.

The image processing unit 2b is provided with a CPU, ROM, RAM image processor and the like, and is connected to the measuring unit 2a by means of an electric signal cable, as shown in FIG. 3. Furthermore, the image processing unit 2b captures the particle image from the video camera 29 of the measuring unit 2a, and subjects the captured particle image to image processing. The result of the image processing is to excise a partial image containing the image of a particle included in the particle image. The image processing unit 2b is connected to the control unit 2c through an electric signal cable, and connected to the data processing apparatus 3 through an electric signal cable 7.

The control unit 2c is provided with a CPU 29a, ROM 29b, RAM 29c, and I/O interface 29d. The CPU 29a is capable of executing computer programs recorded in ROM 29b, and computer programs loaded in the RAM 29c. The ROM 29b is configured by a mask ROM, PROM, EPROM, EEPROM or the like, and stores the control program 29e executed by the CPU 29a as well as data used by the control program 29e. The RAM 29c is configured by an SRAM, DRAM or the like. The RAM 29c is used as a work area for the CPU 29a when executing the control program 29e stored in the ROM 29b.

Figure 5:
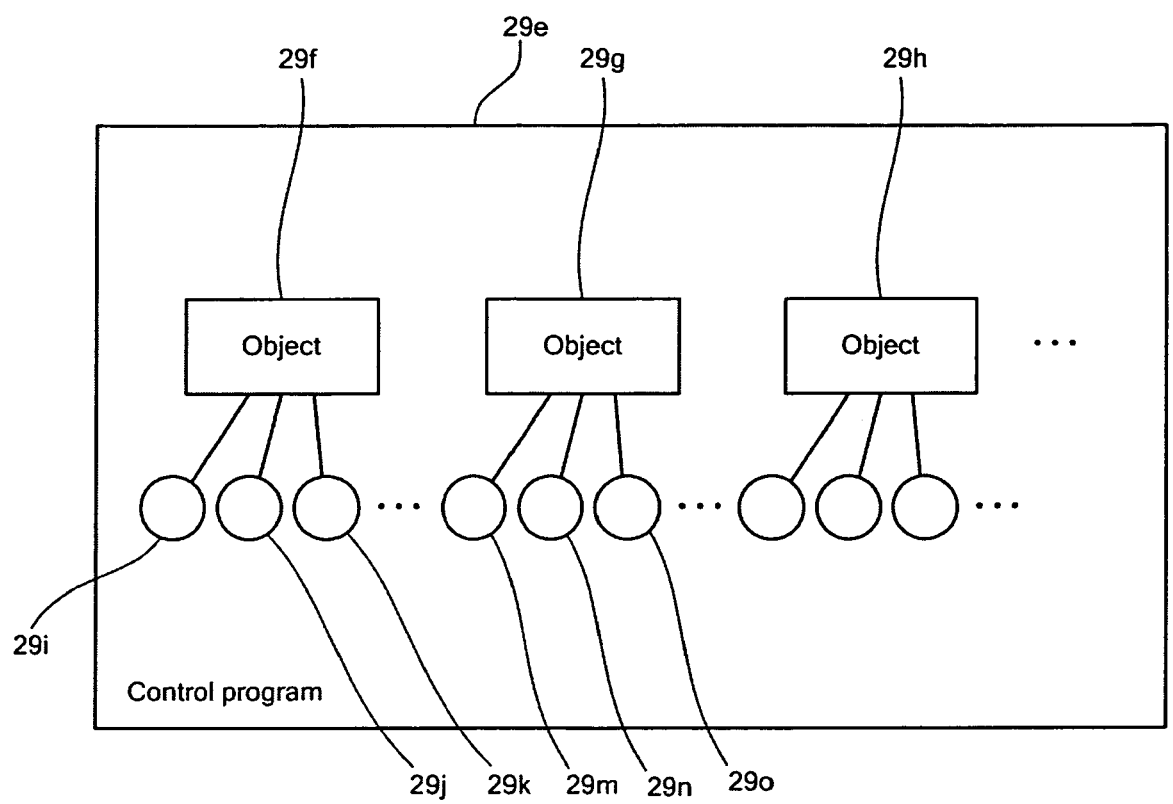
FIG. 5 is a schematic view showing the structure of the control program of an embodiment of the present invention.

FIG. 5 is a schematic view showing the structure of the control program 29e. The control program 29e is a computer program created by object oriented programming, and has a plurality of objects 29f-29h. The object 29f is called 'MeasSetting,' and has the function of performing various settings of the measuring unit 2a. The object 29g is called 'LimResult,' and has the function of storing the measurement results of the measuring unit 2a. The object 29h is called 'PASetting,' and has the function of setting the analysis conditions of the measuring unit 2a. The objects 29f-29h are among the objects included in the control program 29e; other objects in the control program 29e include, for example, objects with the functions of reading pressure values of each component of the measuring unit 2a from a plurality of pressure sensors (not shown in the drawings) included in the measuring unit 2a, as well as other objects, and these and other objects are omitted to simplify the description. The operation of the particle analyzer 2 is controlled, and the measurement results of the particle analyzer 2 are saved by the functions of the objects 29f-29h.

The objects 29f-29h have various properties (attributes), and the properties can be set from the data processing apparatus 3 in a manner described later. In this case the object 29f has properties 29i-29k, and the object 29g has properties 29m-29o.

The property 29i is called 'OLensUnit,' and is used to set the object lens 28a. The property 29i has setting values of [1], [2], and [3]; the magnification is set at 5× at setting value [1], magnification is set at 10× at setting value [2], and magnification is set at 20× at setting value [3]. The property 29j is called 'TempTarget,' and is used to set a target temperature of the measuring unit 2a. The property 29j can be set at integer values, for example, when set at a value of [250], the target temperature of the measuring unit 2a is set at 25° C. The property 29k is called 'MaxMeasCount,' and is used to set the number of measurement repetitions. The property 29k can be set at integer values, for example, when set at a value of [2], the measurement is repeated twice.

The property 29m is called 'Density,' and is used to save the particle density data of one measurement result of the particle analyzer 2. The property 29m sets the floating decimal point data, for example, a value of [5000] is set when the particle density of the measurement result is 5000. The property 29n is called 'DSSizeRatio,' and is used to save the small particle ratio data of one measurement result of the particle analyzer 2. The property 29n sets the floating decimal point data, for example, a value of [20.5] is set when the particle ratio of the measurement result is 20.5. The property 29o is called 'DMSizeRatio,' and is used to save the intermediate particle ratio data of one measurement result of the particle analyzer 2. The property 29o also sets floating point data.

These properties 29i-29k and 29m-29o are some of the properties of the objects 29f and 29g; although the objects 29f and 29g are provided with other properties, these other properties have been omitted to facilitate the description.

The structure of the data processing apparatus 3 is described below.

Figure 6:
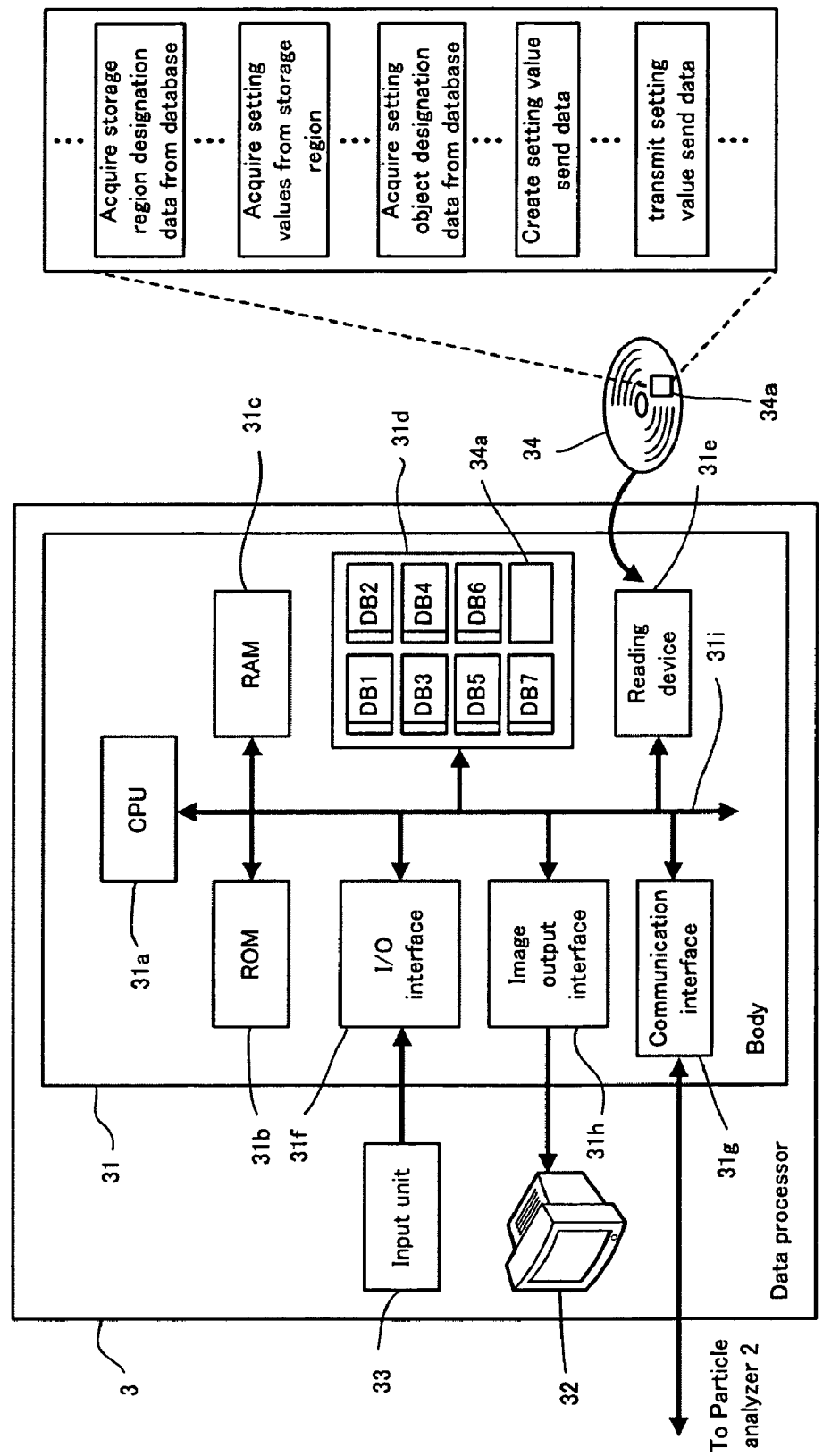
FIG. 6 is a block diagram showing the structure of a data processing apparatus of an embodiment of the present invention.

FIG. 6 is a block diagram showing the structure of a data processing apparatus 3 of an embodiment of the present invention. The data processing apparatus 3 is configured by a computer 3a mainly including a body 31, image display unit 32, and input unit 33. The body 31 is mainly configured by a CPU 31a, ROM 31b, RAM 31c, hard disk 31d, reading device 31e, I/O interface 31f, communication interface 31g, and image output interface 31h, and the CPU 31a, ROM 31b, RAM 31c, hard disk 31d, reading device 31e, I/O interface 31f, communication interface 31g, and image output interface 31h are connected by a bus 31i.

The CPU 31a is capable of executing computer programs recorded in ROM 31b, and computer programs loaded in the RAM 31c. The computer 3a functions as the data processing apparatus 3 when the CPU 31a executes the application program 34a described later.

The ROM 31b is configured by a mask ROM, PROM, EPROM, EEPROM or the like, and stores the computer program executed by the CPU 31a as well as data used by the computer program.

The RAM 31c is configured by an SRAM, DRAM or the like. The RAM 31c is used when reading the computer programs stored in the ROM 31b and on the hard disk 31d. Furthermore, when these computer programs are executed, the RAM 31c is used as the work area of the CPU 31a.

The hard disk 31d accommodates an operating system and application programs and the like, various installed computer programs executed by the CPU 31a, and data used during the execution of these computer programs. An application program 34a, described later, is also installed on the hard disk 31d.

The reading device 31e is configured by a floppy disk drive, CD-ROM drive, DVD-ROM drive or the like, that can read computer programs and data recorded on a portable recording medium 34. The portable recording medium 34 stores the application program 34a that allows a computer to function as the data processing apparatus for a measuring apparatus of the present invention; the computer 3a can read the application program 34a of the present invention from the portable recording medium 34 by the computer 3a, and install the application program 34a on the hard disk 31d.

The application program 34a is not limited to being provided by the portable recording medium 34, inasmuch as the application program 34a may also be provided over an electric communication line (wireless or wire line) from an external device connected to the computer 3a so as to be communication capable. For example, the application program 34a may be stored on the hard disk of a server computer on the Internet, such that the computer 3a can access the server computer and download the application program 34a and install the application program 34a on the local hard disk 31d.

The operating system installed on the hard disk 31d provides a graphical user interface environment, for example, Windows (registered trademark) manufactured by Microsoft Corporation, Inc. (headquartered in the USA). In the following description, the application program 34a of the present embodiment works under the aforesaid operating system.

The application program 34a receives image processing result data from the image processing performed by the particle analyzer 2, executes image processing of partial images included in the received image processing result data, and calculates the particle size (circular equivalent diameter) and roundness of each particle image. Then, The application program 34a also has the functions of displaying the received partial images in a matrix array on the display screen, displaying the particle diameter and roundness of selected partial images, saving the particle size and roundness of the processing results in a database, and creating charts such as scattergrams of predetermined analysis results. The application program 34a is also provided with a function for setting the settings of the particle analyzer 2. The hard disk 31d is also provided with a database DB1 for storing setting values of the basic settings of the particle analyzer 2, database DB2 for storing setting values of the measurement condition settings of the particle analyzer 2, database DB3 for storing setting items of the measurement condition settings of the particle analyzer 2, database DB4 for storing object names and property names of setting objects and the storage regions of the setting values when setting the particle analyzer 2, database DB5 for storing the write destination database name and field name of the setting values and measurement values as well as the read origin object name and property name of the setting values and measurement values when measurement has been performed by the particle analyzer 2, database DB6 for storing the setting values when measurement has been performed by the particle analyzer 2, and database DB7 for storing the measurement values of the particle analyzer 2.

The structure of the database DB1 is described below. FIG. 7 is a schematic diagram showing the structure of the database DB1. As shown in FIG. 7, the database DB1 is a database in table format having a plurality of fields. The database DB1 is called 'SYSTEMM,' and is specified in the process of the application program 34a using the this name. The setting values (parameters) stored in the database DB1 are associated with various characteristic items. The setting items are divided into various types such as [identification number], [blank check], [air pressure source timer] and the like, and the types of items are divided categories such as [system], [measuring unit], [transmission] and the like. In this way the setting values can be divided into three levels of category item, type item, and setting item. Thus, when a user searches the setting values, a target setting value can be easily found by searching the category items, type items and setting items. The database DB1 has an ID field 35a for storing the setting parameter ID, category number field 35b for storing the number of the category item, category item display name field 35c for storing the display name of the category item, type item display name field 35d for storing the display name of the type item, setting item name field 35e for storing the setting item name, setting item display name field 35f for storing the setting item display name, data field 35g for storing setting values, data type field 35h for storing the setting value data type, minimum value field 35i for storing the minimum value of the setting value range, maximum value field 35j for storing the maximum value of the setting value range, and combo list field 35k for storing the items displayed as a combo list. The category number is a number unique to each category item, such that a category item can be specified by this number. The category item display name, type item display name, and setting item display name are the names of the category items, type items, and setting items displayed in the various screens. The category item display name, type item display name, and setting item display name are names that are readily understood by the user at a glance such that the item is understood. Data types are information stipulating the range of numeric values of the data and properties of the object data, that is, integer (Int), long integer (Long), floating decimal (Float), selectable (Sel) and the like. The selectable data type is a parameter having a format that specifies a user selection from a plurality of predefined parameter candidates. The combo list is a collection of parameter candidates that can be set as a parameter by the user, such that the user selects a desired parameter from among the parameter candidates. The data types of the parameters set in the combo list are all selectable. In the database DB1, a parameter candidates are separated and defined by the symbol "|", as shown in FIG. 7. That is, in the present embodiment, data separated by the symbol "|" are parameter candidates in the combo list field 35k of the database DB1.

Although the database DB1 is also provided with a classification item name field for storing classification names used to specify classifications in the process of the application program 34a, type item name field for storing type item names used for specifying type items in the process of the application program 34a and the like, these fields are omitted to facilitate the description.

FIG. 7 shows part of the database DB1. In the example shown in FIG. 7, a setting value of [2] corresponding to the setting item name "OLensUnit" and setting item display name "object lens unit," and a setting value of [250] correspond to the setting item name "TempTarget" and setting item display name "detection unit target temperature" are respectively stored in the database DB1. The setting item "OLensUnit" is defined as a selectable data type, and the setting value [2] of this item corresponds to [10×], which is the second from the left in the combo menu of [5×], [10×], and [20×] recorded on the combo list. The setting item "TempTarget" defines integer as the data type.

The structure of the database DB2 is described below. FIG. 8 is a schematic diagram showing the structure of the database DB2. As shown in FIG. 8, the database DB2 is provided with a plurality of tables with a plurality of fields. The database DB2 is called "SOPMDT," and the database DB2 is specified by using this name in the process of the application program 34a. In the particle analyzer 2, since the measuring conditions differ depending on the type of sample to be measured, for example, latex, toner and the like, and since the measuring conditions used may change frequently depending on the user, a plurality of measuring conditions (hereinafter referred to as SOP) that are frequently used by the operator are prerecorded such that a user-desired SOP can be selected from among the numerous SOPs in the application program 34a. Thus, a plurality of tables corresponding to the SOPs are provided in the database DB2, and setting data of the particle analyzer 2 are stored in the respective tables. FIG. 8 shows only the tables corresponding to the latex measurement SOP among the numerous tables included in the database DB2. The name "SOPMDT" is used in the process of the application program 34a, such that a table is specified by the ID specifying an SOP at that time. The ID specifying this SOP is stored as a record in the corresponding table. The previously described database DB1 has only one table, and the setting values stored in the table arte used in common by all SOPs.

The respective inherent setting items are associated with the parameters stored in the database DB2. The database DB2 is provided with a setting item name field 36a for storing the name of the setting items, and a data field 36b for storing setting values. Each parameter is associated with a setting item name stored in the setting item name field, so as to be stored in the data field 36b. FIG. 8 shows part of the database DB2. In the example shown in FIG. 8, a setting value of [1] associated with the setting item name "MaxMeasCount" is stored in the database DB2.

The structure of the database DB3 is described below. FIG. 9 is a schematic diagram showing the structure of the database DB3. As shown in FIG. 9, the database DB3 is a database in table format having a plurality of fields. The database DB3 is called "SOPODEDEF," and in the process of the application program 34a this name is used to specify the database DB3. In order to define the setting values recorded in the database DB2, the database DB3 is provided with an ID field 37a for storing the IDs of the setting parameters, database field 37b for storing database names of the storage destination storing the setting values after measurements have ended, setting item name field 37c for storing setting item names, setting item display name field 37d for storing the setting item display names, data type field 37e for storing the data type of the setting value, default value field 37f for storing the default value of the setting value, combo list field 37g for storing the items displayed as a combo list, maximum value field 37h for storing the maximum value of the range of the setting values, and minimum value field 37i for storing the minimum value of the range of the setting values. The data type field 37e and combo list field 37g have the same structures as the previously described data type field 35h and combo list field 35k of the database DB1 and therefore further description is omitted. Although other fields are provided in the database DB2, they are omitted from this description for clarity.

FIG. 9 shows part of the database DB3. In the example shown in FIG. 9, the records of setting item name "MaxMeasCount" and setting item display name "number of repeats" are recorded in the database DB3. The setting item "MaxMeasCount" is defined as a long integer data type, and has a default value [1], and maximum value [999] and minimum value [1] for the range of the setting values.

The structure of the database DB4 is described below. FIG. 10 is a schematic diagram showing the structure of the database DB4. As shown in FIG. 10, the database DB4 is a database in table format having a plurality of fields. The database DB4 is called "CMDMSU," and the database DB4 is specified by using this name in the process of the application program 34a. The database DB4 is provided with an ID field 38a for storing the ID of the setting item for transmitting the transmission item to the particle analyzer 2, item display name field 38b for storing the display name of the transmission item, input table field 38c for storing the table name of the input origin (read origin) of the setting value, input item field 38d for storing the setting item of the input origin in the table, object field 38e for storing the object name of the setting object, property field 38f for storing the property name of the setting object in the aforesaid object, flag 1 field 38g, flag 2 field 38h, and flag 3 field 38i for storing the flags related to the setting timing. Although other fields are provided in the database DB4, they are omitted from this description for clarity.

The IDs stored in the ID field 38a are numbers indicating the transmission sequence of the transmission items; when transmitting the data including the setting values to the particle analyzer 2 while the application program 34a is executing, the CPU 31a reads the data and setting values specifying the setting object according to the ID sequence and transmits this information to the particle analyzer 2. The item display names stored in the item display name field 38b are names that allow the user to comprehend the transmission item at a glance. The item display names are displayed in association with a code in a window or the like for recording new data and data updates to the database DB4. The input table names are data that specifies the database from which the setting value object was read; object database names are stored as "SYSTEMM" in the case of database DB1, and "SOPCODEDEF" in the case of database DB3. More specifically, in the present embodiment, when the input table name is "SOPCODEDEF," the database DB3 is not the reading object, rather the database DB2 is the reading object. The input item names are data designating the setting item of the read setting value among the databases specified by the input table name, and the setting item name is stored in the database. The storage region in which a setting value is stored is specified by the input table name and input item name. The object name stored in the object field 38e corresponds to the name of the object in the control program 29e of the particle analyzer 2, and the property name stored in the property field 38f corresponds to the name of the property of the object. The setting object of the setting value can be specified by the object name and the property name. That is, the transmission item object name, and property of the object specified by the property name are set by the setting values stored in the storage regions specified by the previously described input table name and input item name.

The flag 1 stored in the flag 1 field 38g indicates whether or not the corresponding setting item is set when measurement starts; when the flag 1 is set at [1], that is, when the setting item has [1] stored in the flag 1 field 38g, the setting item has been set when measurement starts. When the flag 1 is set at [0], that is, when the setting item has [0] stored in the flag 1 field 38g, the setting item is not set when measurement starts. The flag 2 stored in the flag 2 field 38h indicates whether or not the corresponding setting item is set when the particle analyzer 2 starts; when the flag 2 is set at [1], that is when the setting item has [1] stored in the flag 2 field 38h, the setting item is set when the particle analyzer 2 starts. When the flag 2 is set at [0], that is, when the setting item has [0] stored in the flag 2 field 38h, the setting item is not set when the particle analyzer 2 starts. The flag 3 stored in the flag 3 field 38i indicates whether or not the setting item is set when the particle analyzer 2 is reset. When the flag 3 is set at [1], that is, when the setting item has [1] stored in the flag 3 field 38i, the setting item is set when the particle analyzer 2 is reset. When the flag 3 is set at [0], that is, when the setting item has [0] stored in the flag 3 field 38i, the setting item is not set when particle analyzer 2 is reset.

FIG. 10 shows part of the database DB4. In the example shown in FIG. 10, the input table name "SOPCODEDEF" and input item name "MaxMeasCount" transmission item, input table name "SYSTEMM" and input item name "TempTarget" transmission item, and input table name "SYSTEMM" and input item name "OLensUnit" transmission item are respectively recorded in the database DB4. The input item name "MaxMeasCount" transmission item specifies the "total number of repetitions" by its name, and the object name is "MeasSettings," and the property name is "MaxMeasCount." The setting item "MaxMeasCount" has all three flags 1-3 set at [1]. The input item name "TempTarget" transmission item specifies the "detection unit target temperature" by its name, and the object name is "MeasSettings," and the property name is "TempTarget." The setting item "TempTarget" has all three flags 1-3 set at [1]. The input item name "OLensUnit" transmission item specifies the "object lens unit" by its name, and the object name is "MeasSettings," and the property name is "TempTarget." The setting item "TempTarget" has all three flags 1-3 set at [1].

The structure of the database DB5 is described below. FIG. 11 is a schematic diagram showing the structure of the database DB5. As shown in FIG. 11, the database DB5 is a database in table format having a plurality of fields. The database DB5 is called "CMDSAU," and the database DB5 is specified by using this name in the process of the application program 34a. The database DB5 is provided with is provided with ID field 39a for storing the reception item, that is the item ID received from the particle analyzer 2, item display name field 39b for storing the display name of the reception item, output table field 39c for storing the table name of the output destination (read destination) of the setting value when measurement results are received from the particle analyzer 2, output field 39d for storing the field name of the of the output destination in the table, object field 39e for storing the object name of the control program 29e, and property field 39f for storing the property name of the object. Although other fields are provided in the database DB5, they are omitted from this description for clarity.

The item display names stored in the item display name field 38b are names that allow the user to comprehend the reception item at a glance. The item display names are displayed in association with a code in a window or the like for recording new data and data updates to the database DB5. The output field names are data designating the database of the reception data read object, and stores the name of the object database, which is "MRESULT in the case of database DB6, and "ANARESULT" in the case of database DB7. The output field names are data designating the field of the reception data write object among the databases specified by the output table name, and stores the field name. The storage regions in which the reception data are stored are specified by the output table name and the output field name. The object name stored in the object field 39e corresponds to the name of the object in the control program 29e of the particle analyzer 2, and the property name stored in the property field 39f corresponds to the name of the property of the object. The origin of the read reception data is specified by the object name and property name. That is, the data read from the property of the object specified by the object name and property name included in the reception item are stored in the storage region specified by the previously described output table name and output field name.

FIG. 11 shows part of the database DB5. In the example shown in FIG. 11, the object name "MeasSettings" and property name "MaxMeasCount" records, object name "MeasSettings" and property name "TempTarget" records, object name "MeasSettings" and property name "OLensUnit" records, object name "LimResult" and property name "Density" records, object name "LimResult" and property name "DSSizeRatio" records, and object name "LimResult" and property name "DMSizeRatio" records are respectively stored in the database DB5. The property name "MaxMeasCount," "TempTarget," and "OLensUnit" records set such that the respective output table name is "MRESULT," and the output field name is "MetaData." Furthermore, the property name "Density" record is set such that the output table name is "ANARESULT," and the output field name is "Density." The property name "DSSizeRatio" record is set such that the output table name is "ANARESULT," and the output field name is "DSSizeRatio." The property name "DMSizeRatio" record is set such that the output table name is "ANARESULT," and the output field name is "DMSizeRatio."

Figure 12:
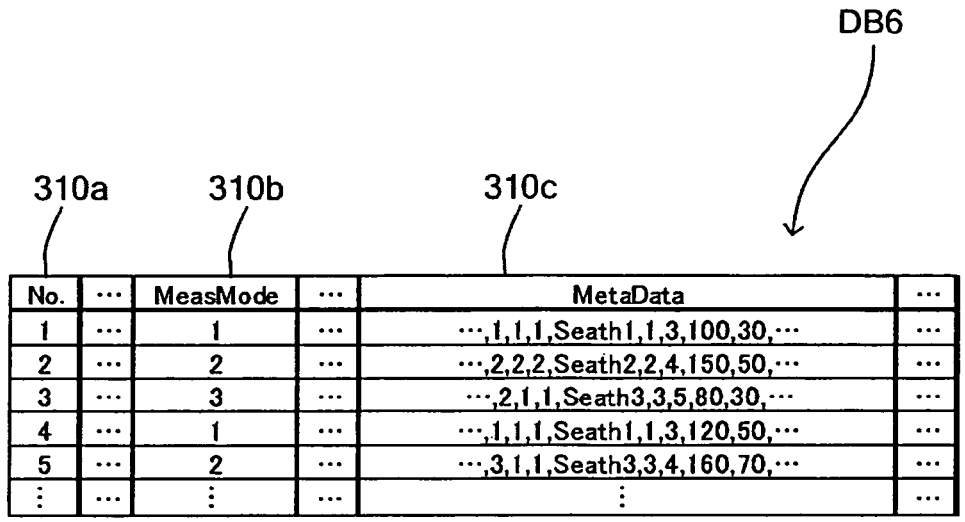
FIG. 12 is a schematic view showing the structure of a database DB6 of an embodiment of the present invention.

The structure of the database DB6 is described below. FIG. 12 is a schematic diagram showing the structure of the database DB6. As shown in FIG. 12, the database DB6 is a database in table format having a plurality of fields. The name of the database DB6 is "MRESULT," and the database DB6 is specified using this name in the process of the application program 34a. The database DB6 stores the various setting values of the particle analyzer 2 when measurements are performed by the particle analyzer 2. FIG. 12 shows part of the database DB6. In the example shown in FIG. 12, the database DB6 is provided with a record number field 310a for storing record numbers, measurement mode field 310b for storing the measurement modes, and metadata field 310c for storing the dataset of the setting values. The database DB6 creates new records of the measurements received from the particle analyzer 2 as described later. The record numbers in the generation sequence participate in these records, and are stored in the record number field 310a. The measurement mode field 310b is called "MeasMode," and the metadata field 310c is called "MetaData." The measurement mode field 310b and metadata field 310c are specified using these names in the process of the application program 34a. Data indicating the measurement mode when measurement is performed by the particle analyzer 2 are stored in the measurement mode field 310b. Furthermore, a collection of data of the setting values for number of repetitions, MAX count number, sheath fluid used, sheath fluid ID, target pressure, syringe speed and the like delineated by commas are stored in the metadata field 310c.

Figure 13:
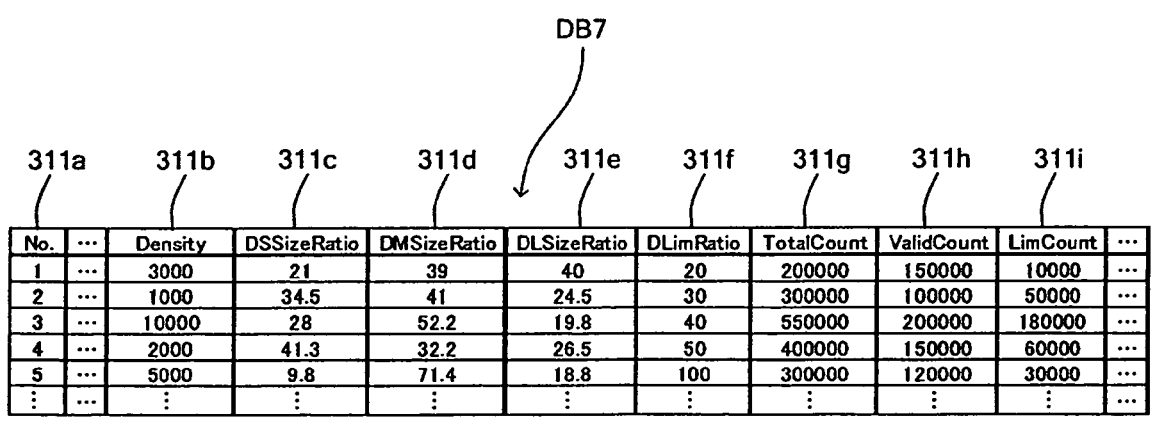
FIG. 13 is a schematic view showing the structure of a database DB7 of an embodiment of the present invention.

The structure of the database DB7 is described below. FIG. 13 is a schematic diagram showing the structure of the database DB7. As shown in FIG. 13, the database DB7 is a database in table format having a plurality of fields. The name of the database DB7 is "ANARESULT," and the database DB7 is specified using this name in the process of the application program 34a. The database DB7 stores the various measurement values of the particle analyzer 2 when measurements are performed by the particle analyzer 2. FIG. 13 shows part of the database DB7. In the example shown in FIG. 13, the database DB7 is provided with a record number field 311a for storing record numbers, particle density field 311b for storing the particle densities, small particle ratio field 311c for storing the small particle ratio, intermediate particle ratio field 311d for storing the intermediate particle ratio, large particle ratio field 311e for storing the large particle ratio, particle limit ratio field 311f for storing the particle limit ratio, detected particle number field 311g for storing the detected number of particles, valid analysis number field 311h for storing the valid analysis number, and the limit particle number field 311i for storing the limit particle number. The database DB7 creates new records of the measurement results received from the particle analyzer 2 as described later. The record numbers in the generation sequence participate in these records, and are stored in the record number field 311a. The particle density field 311b is called "Density," the small particle ratio field 311c is called "DSSizeRatio," the intermediate particle ratio 311d is called "DMSizeRatio," the large particle ratio field 311e is called "DLSizeRatio," the particle limit ratio field 311f is called "DLimRatio," the detected particle number field 311g is called "TotalCount," the valid analysis number field 311h is called "ValidCount," and the limit particle number field 311i is called "LimCount." The particle density mode field 311b, small particle ratio 311c, intermediate particle ratio field 311d, large particle ratio field 311e, particle limit ratio field 311f, detected particle number field 311g, valid analysis number field 311h, and limit particle number field 311i are specified using these names in the process of the application program 34a.

The I/O interface 31f is configured by an analog interface including a serial interface, such as a USB, IEEE1394, RS-232C or the like, parallel interface, such as, for example, a SCSI, IDE, IEEE1284 or the like, D/A converter, and A/D converter and the like. The input unit 33 configured by a keyboard and mouse is connected to the I/O interface 31f, such that data can be input to the computer 3a when a user operates the input unit 33.

The communication interface 31g is, for example, an Ethernet (registered trademark) interface, and is connected to the particle analyzer 2 so as to be capable of data communication through an electric signal cable 7. The computer 3a is capable of sending and receiving data to and from the particle analyzer 2 using a predetermined communication protocol by means of this communication interface 31g.

The image output interface 31h is connected to the image display unit 32, which is configured by an LCD, CRT or the like, such that image signals corresponding to the image data received from the CPU 31a are output to the image display unit 32. The image display unit 32 displays images (screens) in accordance with the input signals.

Figure 14:
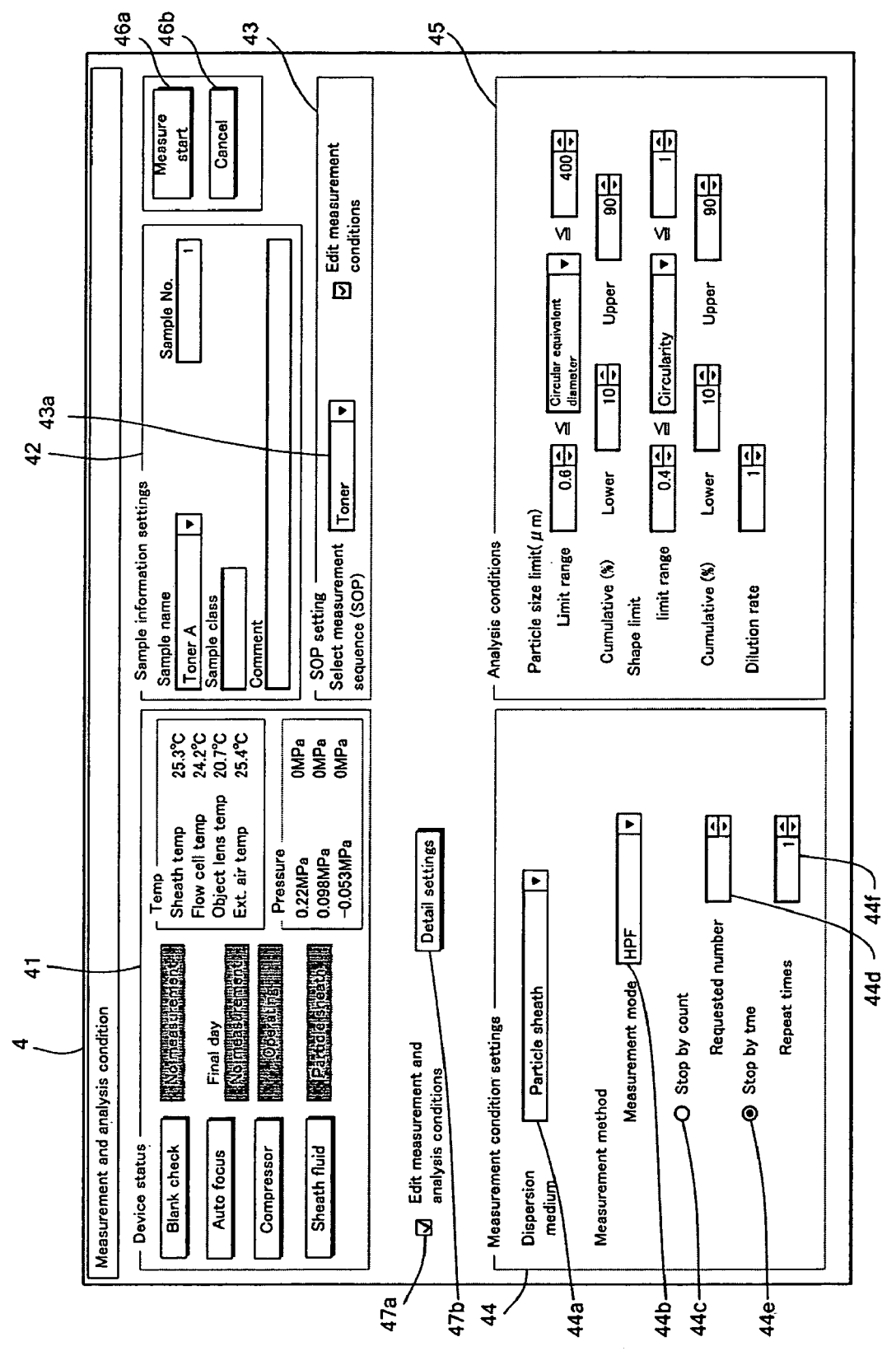

The operation of the measuring system 1 of present embodiment of the invention is described below. the application program 34a can be started when the user operates the input unit 33 of the computer 3a by clicking an icon, menu, button or the like associated with the start command of the application program 34a, or inputting a command to start the application program 34a. In this state, when a user performs a predetermined operation on the data processing apparatus 3, a window described below is displayed on the image display unit 32 of the data processing apparatus 3. FIG. 14 is a schematic view showing a window for setting the measurement and analysis conditions. As shown in FIG. 14, this window is provided with a status setting region 41 for displaying the button types for setting the status of the apparatus, sample information setting region 42 for displaying input boxes and combo boxes for setting the information relating to the measurement sample, SOP setting region 43 for displaying the combo box 43a for setting the SOP, measurement condition setting region 44 for displaying the combo box, input box, and radial buttons for setting the measurement conditions, and analysis condition setting region 45 for displaying the combo box for setting the analysis conditions. This window is also provided with a measurement start button 46a to specify starting measurement, cancel button 46 for canceling a setting, check box 47a for enabling detailed settings of the measurement and analysis conditions, and detailed setting start button 47b for displaying a window for detailed setting of the measurement and analysis conditions. When display of window 4 is specified, the CPU 31a loads data from the databases DB2 and DB3 into the RAM 31c, new data are then displayed in the combo box and input box at this time, and the combo box selection items are set.

In the window 4, it is possible to set some settings among the simple measurement conditions settings, and each type of setting item. The combo box 43a is provided in the SOP setting region 43 in the window 4. A list of selected items (combo list) is displayed in a pulldown menu by positioning the mouse pointer displayed on the screen over a triangular arrow button provided at the left end of the combo box 43a by the user moving the mouse provided with the input unit 33, and left clicking the left mouse button once. This item can be selected by the user left-clicking one desired item among the selectable items using the mouse. FIG. 14 shows the selection of the SOP with the name "Latex." When the user has selected another item in the combo list 43a, the setting values corresponding to the selected item are displayed in the combo box and input box, and the combo list of the combo box is reset.

The measurement condition setting region 44 in window 4 is provided with a combo box 44a for specifying a dispersion medium (sheath fluid), combo box 44b for specifying a measurement mode, radial button 44c for specifying a total count, combo box 44d for specifying a total count number, radial button 44e for selecting a time count, and combo box 44f for specifying number of repeats. Selected items from the combo box 44a can be shown in a pulldown display when the user performs the previously described operation so as to specify a desired sheath fluid. A combo list (|LPF|HPF|LPF->HPF|) corresponding to the setting item name "MeasMode" in database DB3 is set in the measurement mode combo box 44b. In this case, [LPF] is a low magnification measurement mode using the 0.5× relay lens. Furthermore, [HPF] is a high resolution measurement mode using the 2× relay lens, and [LPF->HPF] is a measurement mode for changing from LPF to HPF while measurement is on-going. The radial buttons 44c and 44e are configured such that only one or the other can be set. FIG. 14 shows an example in which the time count is set. As shown in the drawing, when the time count is set, the combo box 44d is displayed in a light color (gray), and cannot be used since it does not respond to a user mouse click; however, the combo box 44f is displayed in a normal color (dark color), and a number, for example, 2 to 9999 can be set for the number of measurements. Conversely, when the total count is set, the combo box 44d is displayed in a dark color, and the combo box 44f is displayed in a light color. The combo box 44d can set the total count number (total number of particles measured) in a range, for example, from 1 to 30000.

The newly set content in window 4 is not reflected in the databases DB2 and DB3, such that only the content loaded in the RAM 31c is changed. After the user inputs the necessary data for measurement in the window 4 and left-clicks the measurement button 46a, the set conditions (setting values) are set in the particle analyzer 2, and it is then possible to specify that measurement starts.

Figure 15:
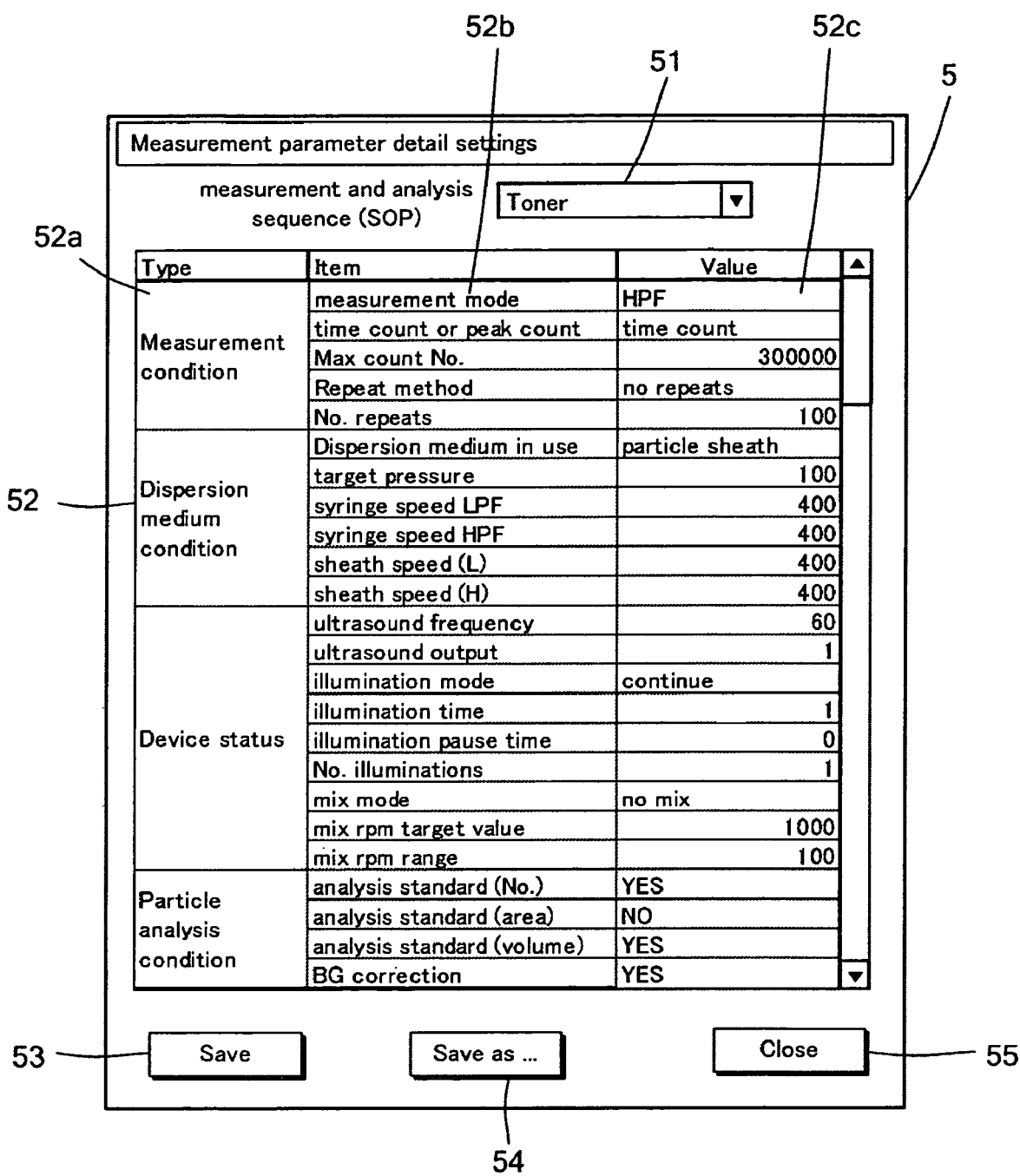
FIG. 15 is a schematic view showing a window for detailed settings of measurement conditions and the like in the application program of an embodiment of the present invention.

When a user checks the check box 47a and left-clicks the detailed setting start button 47b in the window 4, a detailed setting window that described later is displayed on the screen of the data processing apparatus 3. FIG. 15 is a schematic diagram shown a window for performing detailed settings of the measurement conditions and the like. When the detailed setting start button 47b is left-clicked, the CPU 31a creates a window 5 using the data from the databases DB2 and DB3 loaded in the RAM 31c, and displays this window on the screen. As shown in FIG. 15, the window 5 is provided with a combo box 51 for specifying the SOP, table 53 of setting values, button 53 for specifying address save, button 54 for specifying new save, and button 55 for closing the window 5.

The combo box 51 has a triangular arrow button on the left end of the box, and when that arrow button is left-clicked a pulldown combo list of defined SOPs is displayed. The user can select a desired SOP from the list by left-clicking on the desired SOP. When an SOP has been selected, the setting values corresponding to the selected SOP among the data of the database DB2 are displayed in the table 52. The table 52 is provided with a type field 52a for displaying the type name of the setting item, setting item display name field 52*b* for displaying the setting item display name, and setting value field 52*c* for displaying the setting value. The type name recorded in the database DB3 is displayed in the type field 52*a*, and the setting item display name recorded in the setting item display name field 37*d* (refer to FIG. 9) of the database DB3 is displayed in the setting item display name field 52*b*. The setting value recorded in the data field 36*b* (refer to FIG. 8) of the database DB2 is displayed in the setting value field 52*c*.

The cells of the setting value field 52*c* can be set for data input when a user double clicks (two consecutive left clicks) on a target cell. When the user changes the setting value, the user double clicks on the cell and enters the new setting value. The CPU 31*a* updates the data in the RAM 31*c* with the setting value just input. When the button 53 is left-clicked after the setting value has been changed, the CPU 31*a* updates the content (data stored in the RAM 31*c*) after the table data has been changed in the database DB2. When the button 54 is left-clicked after the setting value has been changed, the CPU 31*a* creates a new table with changed content (data stored in the RAM 31*c*) in the database DB2. When the button 55 is left-clicked, the CPU 31*a* closes the window 5. In this way the user records data to the databases DB2 and DB3, and performs data updates.

While the application program 34*a* is executing, the window described below is displayed on the image display unit 32 of the data processing apparatus 3 by means of a predetermined operation of the data processing apparatus 3 by the user. FIG. 16 is a schematic diagram of a window for performing basic settings of the particle analyzer 2. When this operation is performed, the CPU 31*a* creates a window 6 using the data of the database DB1 loaded in the RAM 31*c*, and displays the window on the screen. As shown in FIG. 16, this window 6 is provided with a setting value table 61, button 62 for specifying printing, button 63 for specifying outputting of the setting values to a file, button 64 for saving the setting values, and button 66 for closing the window 6 without saving the setting values.

The table 61 is provided with a classification item display name field 61*a* for displaying the classification item display name of the setting item, type item display name field 61*b* for displaying the type item display name, setting item display name field 61*c* for displaying the setting item display name, and setting value field 61*d* for displaying the setting value. The classification item display name recorded in the classification item display name field 35*c* (refer to FIG. 7) of the database DB1 is displayed in the classification item display name field 61*a*, the type item display name recorded in the type item display name field 35*d* (of the database DB1 is displayed in the type item display name field 61*b*, and the setting value display name recorded in the setting value display name field 35*f* of the database DB1 is displayed in the setting value display name field 61*c*. The setting value recorded in the data field 35*g* of the database DB1 is displayed in the setting value field 61*d*.

The cells of the setting value field 61*d* allow data to be entered when a user double clicks on the object cell. When the user changes the setting value, the user double clicks on the cell and enters the new setting value. The CPU 31*a* updates the data in the RAM 31*a* with the setting value just input. When the button 64 is left-clicked after the setting value has been changed, the CPU 31*a* updates the content (data stored in the RAM 31*c*) after the table data have been changed in the database DB1. When the button 62 is left-clicked, the CPU 31*a* sends instructions to print the content of the table 61 to a printer connected to the data processing apparatus 3 through an electric signal cable, such as a USB cable or the like. In this way the user can print the basic settings. Furthermore, when the button 63 is left-clicked, the CPU 31*a* outputs the content of the table 61 (data stored in the RAM 31*c*) to, for example, a CSV format file. When the button 65 is left-clicked, the CPU 31*a* closes the window 6. In this way the user records data to the databases DB1, and performs data updates.

Although detailed description of the databases DB4-DB7 is omitted, these databases are configured such that can be recorded and updated by the same process described above. A user can also record and edit the data of the databases DB1-DB7 using other database software, spreadsheet software, text editors and the like as well as record data and update data of the databases DB1-DB7 using the functions of the application program 34*a*.

Figure 17:
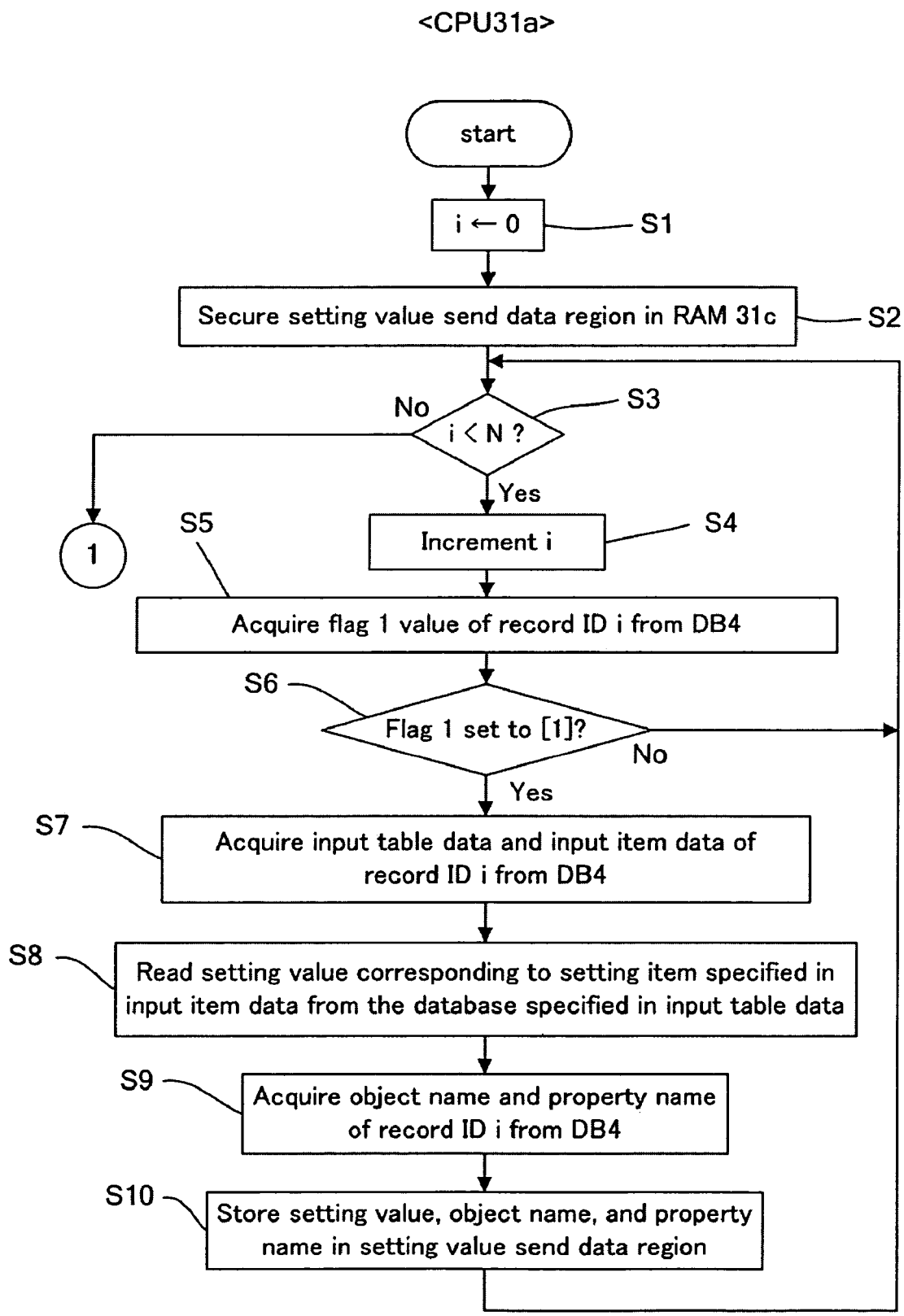
FIG. 17 is a flow chart showing the operation flow when sample measurement starts in the particle analyzer in the measuring system of an embodiment of the present invention.
Figure 18:
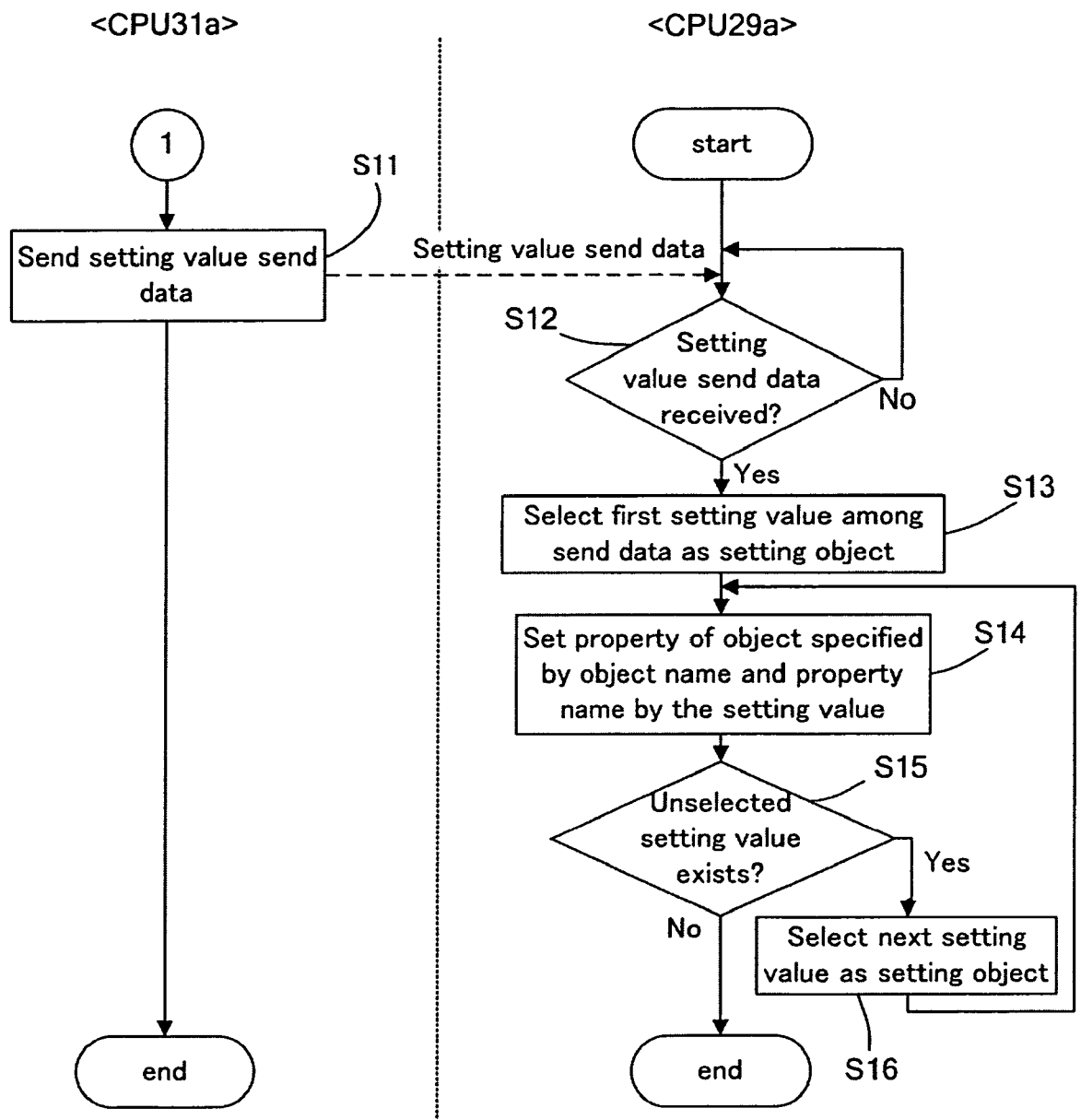
FIG. 18 is a flow chart showing the operation flow when sample measurement starts in the particle analyzer in the measuring system of an embodiment of the present invention.

The operation of the measuring system 1 is described below when the sample measurement is started by the particle analyzer 2. FIGS. 17 and 18 are flow charts showing the flow of the operation of the measuring system 1 in this case. When the measurement start button 46*a* (refer to FIG. 14) is left-clicked in window 4 and the measurement start instruction is received from the user, the CPU 31*a* sets the variable i representing the transmission item ID to [0] (step S1), and secures the regions (hereinafter referred to as 'setting value transmission data region') for creating transmission data (hereinafter referred to as 'setting value transmission data') to be sent to the RAM 31*c* (step S2). Next, the CPU 31*a* determines whether or not the variable i is less than the ID maximum value N recorded in the ID field 38*a* (refer to FIG. 10) of the database DB4 (step S3), and when the value of the variable i is less than N (step S3: YES), the value of the variable i is incremented by [1] (step S4). Then, the CPU 31*a* reads the data of the flag 1 field 38*g* from the same ID as the variable i value from the database DB4 (step S5), and determines whether or not the data is [1] (step S6). As described above, the flag 1 indicates whether or not the setting value of this record is set at the measurement start time. When the flag 1 is set at [1] (step S6: YES), the CPU 31*a* executes the processes of step S7 and subsequent steps, whereas when the flag 1 is set at [0] (step S6: NO), the process returns to step S3.

Then, the CPU 31*a* reads the data of the input table field 38*c* and input item field 38*d* from the same ID as the variable i value from the database DB4 (step S7). For example, the CPU 31*a* reads the input table data "SOPCODEDEF" and the input item data "MaxMeasCount" from the database DB4 when the value of the variable i is [7], and reads the input table data "SYSTEMM" and input item data "TempTarget" from the database DB4 when the value of the variable i is [57] (refer to FIG. 10). Next, the CPU 31*a* reads the setting values corresponding to the setting item specified by the input item data of the database specified by the input table data acquired in the process of step S7 (step S8). In the process of step S8, when the input data is "SOPCODEDEF," the setting values are not read from the database DB3, but rather are read from the database DB2. That is, when the value of the variable i is [7], the CPU 31*a* reads the setting value [1] that corresponds to the setting item "MaxMeasCount" from the database DB2. When the value of the variable i is [57], the CPU 31*a* reads the setting value [250] that corresponds to the setting item "TempTarget" from the database DB1. In the process of step S8, although the data read from the database DB1 are the setting values read from the database DB1 stored on the hard drive 31*d*, the data read from the database DB2 are not the setting values from the database DB2 of the hard disk 31*d*, but rather are the setting values stored in the RAM 31*c* while the window 4 is open.

Then, the CPU 31a reads the data of the object field 38e and property field 38f from the same ID as the variable i value from the database DB4 (step S9). For example, the CPU 31a reads the object name "MeasSettings" and property name "MaxMeasCount" from the database DB4 when the value of the variable i is [7], and reads the object name "MeasSettings" and property name "TempTarget" from the database DB4 when the value of the variable i is [57] (refer to FIG. 10).

Then, the CPU 31a associates the setting values read in step S8, and the object name and property name read in step S9, and writes the data to the setting value transmission data region of the RAM 31c (step S10). In the process of step S10, the new setting value, object name, and property name are added at the end of the setting value transmission data created in the previous process. Thus, when the value of the variable i is [7], [1], "MeasSettings," and "MaxMeasCount" data are added to the end of the data written in processes from variable i value [1] to [6]. When the value of the variable i is [57], [250], "MeasSettings," and "TempTarget" data are added to the end of the data written in processes from variable i value [1] to [56]. After the process of step S10 ends, the CPU 31a returns the process to step S3.

When the value of the variable is N or greater in step S3 (step S3: NO), the CPU 31a sends the setting value transmission data created in the previous process to the particle analyzer 2 (step S11). When the setting value transmission data are received from the data processing apparatus 3 (step S12: YES), the CPU 29a of the particle analyzer 2 selects one setting value (initial setting value among the setting value transmission data) among the setting values included in the setting value transmission data as the setting object (step S13). Then, the CPU 29a sets the property of the object specified by the object name and property name associated with the object setting value by the setting value (step S14). Pursuant to the example, the property 29k (property name "MaxMeasCount") of the object 29f (object name "MeasSettings") is set at [1], and the property 29j (property name "TempTarget") of the object 29f is set at [250]. Then, the CPU 29a determines whether or not a setting value that was not selected as a setting object is among the setting value transmission data (step S15), and when such as setting value exists (step S15: YES), the next setting value is selected as the setting object (step S16), whereupon the process returns to step S14. When a setting value that was not selected as a setting object is not among the setting value transmission data in step S15 (step S15: NO), the CPU 29a ends the process.

Although the process has been described at the start if the sample measurement by the particle analyzer 2, the settings of the objects and properties of the same control program 29e are also executed when the particle analyzer 2 is started and reset. At startup of the particle analyzer 2, the setting value transmission data is not created by the setting value with a flag 1 set at [1] at the start of measurement, rather the setting value transmission data is created by the setting value with a flag 2 set at [1]. When the particle analyzer 2 is reset, the setting value transmission data is created by a setting value with the flag 3 set at [1]. In the setting process at startup or reset of the particle analyzer 2, the use of the flag 2 or flag 3 rather than the flag 1 is identical to the process at the start of measurement, and therefore further description is omitted.

Figure 19:
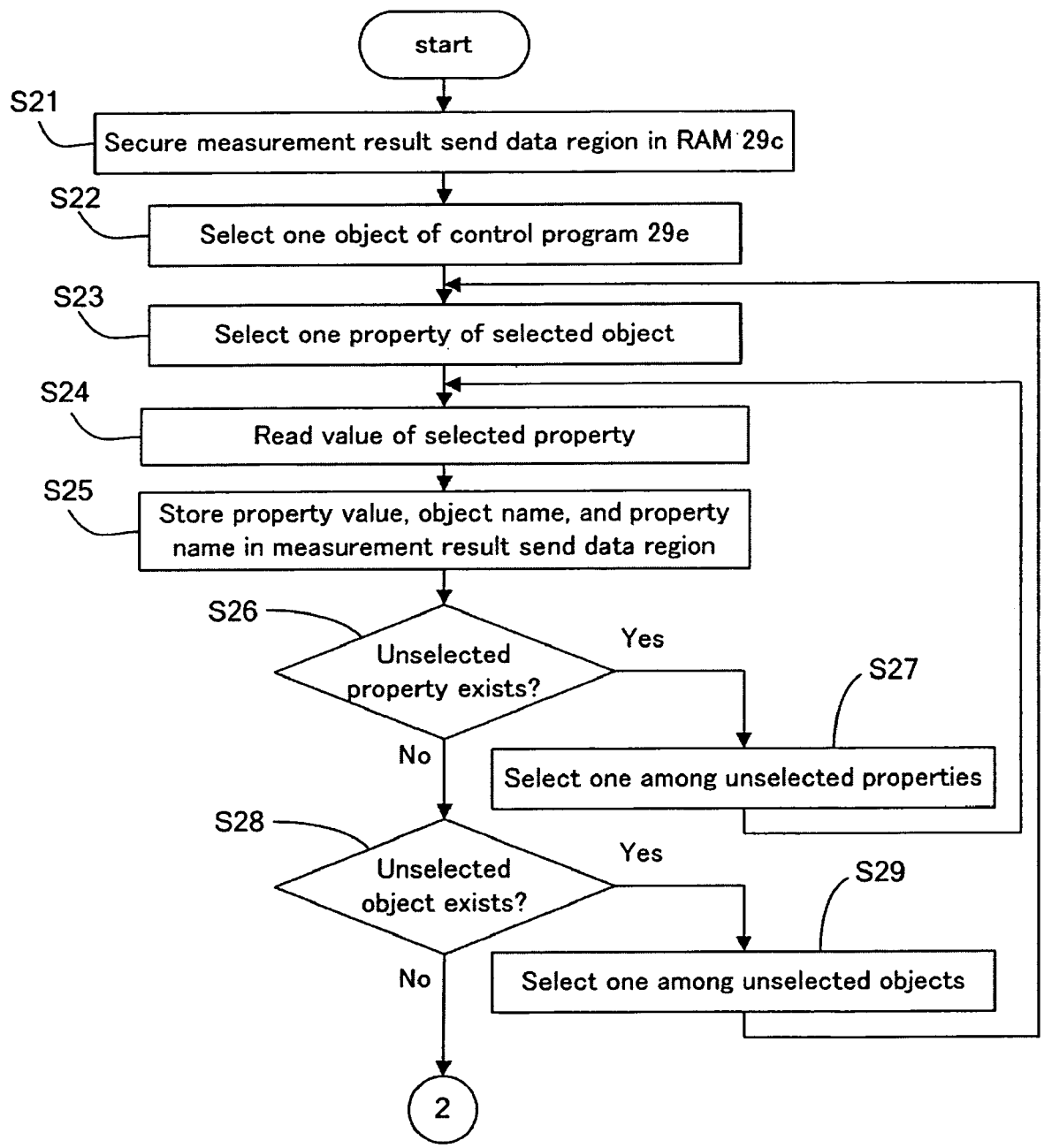
FIG. 19 is a flow chart showing the operation flow when sample measurement ends in the particle analyzer in the measuring system of an embodiment of the present invention.
Figure 20:
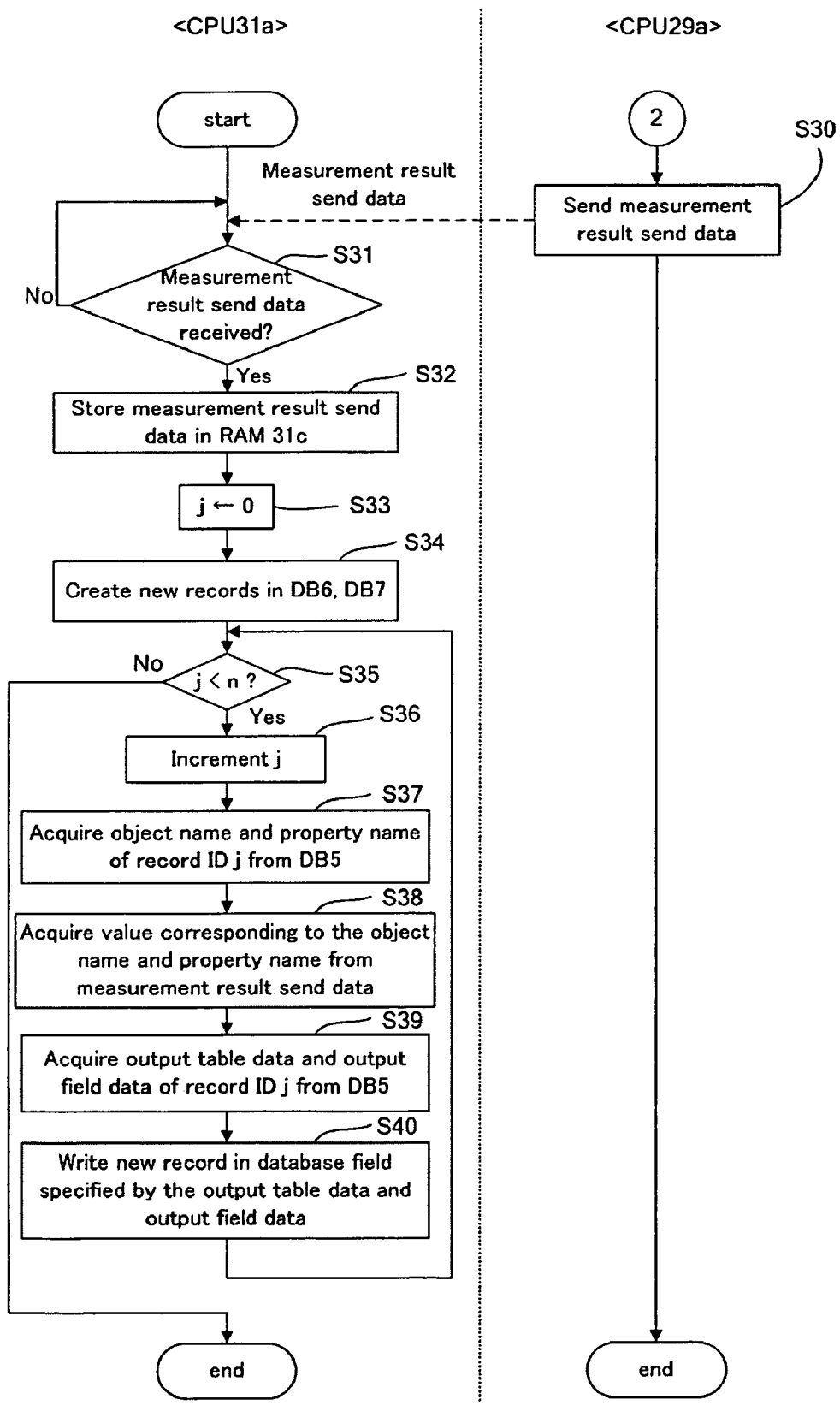
FIG. 20 is a flow chart showing the operation flow when sample measurement ends in the particle analyzer in the measuring system of an embodiment of the present invention.

The operation of the measuring system 1 when the measurement by the particle analyzer 2 has ended is described below. FIGS. 19 and 20 are flow charts showing the flow of the operation of the measuring system 1 in this case. When the sample measurements have ended, the CPU 29a of the particle analyzer 2 secures the region (hereinafter referred to as 'measurement result transmission data region') for creating the transmission data (hereinafter referred to as 'measurement result transmission data') in the RAM 29c. Then, the CPU 29a selects one object of the control program 29e (step S22), then selects one property of this object (step S23). The value of the selected property is read (step S24), and this value and the name of the selected object and the name of the selected property are written to the measurement result transmission region (step S25). In the process of step S26, the new value, object name, and property name are added to the end of the measurement result transmission data created in the previous process. For example, when the property 29i (property name "OLensUnit") of the object 29f (object name "MeasSettings") is selected, the value (for example, [2]) of the property 29i at this time is read, and "MeasSettings," MaxMeasCount," and [2] data are added to the end of the measurement result transmission data during creation.

The CPU 29a determines whether or not as yet unselected properties exist for the selected object (step S26), and when unselected properties exists (step S26: YES), one of the unselected properties is selected (step S27), and the process returns to step S24. When an as yet unselected property of the selected object does not exist and all properties of the selected object have been selected in step S26 (step S26: NO), the CPU 29a determines whether or not an unselected object exists in the control program 29e (step S28), and when an unselected object exists (step 28: YES), one of the unselected objects is selected (step S29), and the process returns to step S23. When there are no unselected objects and all objects has been previously selected (step S28: NO), the CPU 29a sends the created measurement result transmission data to the data processing apparatus 3 (step S30). In the following description, a value of [1] associated with the object name "MeasSettings" and property name "MaxMeasCount," a value of [160] associated with the object name "MeasSettings" and property name "TemTarget," a value of [5000] associated with the object name "LimResult" and property name "Density," a value of [9.8] associated with the object name "LimResult" and property name "DSSizeRatio," and a value of [71.4] associated with the object name "LimResult" and property name "DMSizeRatio" data are included in the measurement result transmission data.

When the measurement result transmission data are received from the particle analyzer 2, the CPU 31a of the data processing apparatus 3 stores the measurement result transmission data in the RAM 31c (step S32). Then, the CPU 31a sets the variable j representing the ID of the received item to [0] (step S33), and creates new records in the databases DB6 and DB7 (step S34). Next, the CPU 31a determines whether or not the value of the variable j is less than the ID maximum value n recorded in the ID field 38a (refer to FIG. 11) of the database DB5 (step S35), and when the value of the variable j is less than n (step S35: YES), the value of the variable j is incremented by [1] (step S36).

Then, the CPU 31a reads the data of the object field 39e and property field 39f from the same ID as the variable j value from the database DB5 (step S379). For example, the CPU 31a reads the object name "MeasSettings" and property name "MaxMeasCount" from the database DB5 when the value of the variable j is [7], and reads the object name "MeasSettings" and property name "TempTarget" from the database DB5 when the value of the variable j is [57] (refer to FIG. 10). For example, the CPU 31a reads the object name "LimResult" and property name "Density" from the database DB5 when the value of the variable j is [57], reads the object name "LimResult" and property name "DSSizeRatio" from the database DB5 when the value of the variable j is [178], and reads the object name "LimResult" and property name "DMSizeRatio" from the database DB5 when the value of the variable j is [178].

The CPU 31a then reads the values corresponding to the object name and property name acquired in the process of step S35 from the measurement result transmission data stored in the RAM 31c (step S38). That is, the CPU reads the value [1] corresponding to the object name "MeasSettings" and property name "MaxMeasCount" from the measurement result transmission data when the value of the variable j is [7], and reads the value [5,000] corresponding to the object name "LimResult" and property name "Density" when the value of the variable j is [177].

Then, the CPU 31a reads the data of the output table field 39c and output field 39d from the same ID as the variable j value from the database DB5 (step S39). For example, the CPU 31a reads the output table data "MRESULT" and output field "MaxMeasCount" from the database DB5 when the value of the variable j is [7], and reads the output table data "ANARESULT" and output field "Density" when the value of the variable j is [177] (refer to FIG. 11).

Then, the CPU 31a writes the values read in step S38 to the records newly added to the fields of the database specified by the output table data and output field data read in step S39 (step S40). That is, when the value of the variable j is [7], the CPU 31a appends the adds [1,] by appending a comma to the value [1] in the metadata table 310c within the record (that is, record number 5 in FIG. 12) added to the database DB6 in step S34. This procedure allows a plurality of property values to be delineated commas and collected in the metadata table 310c. When the value of the variable j is [177], the CPU 31a writes the value [5000] in the particle density field 311b within the record (that is, record number 5 in FIG. 13) added to the database DB7 in step S34. After the process of step S40 ends, the CPU 31a returns the process to step S35. When the value of the variable j is n or greater in step S35 (step S35: NO), the CPU 31a ends the process.

According to the aforesaid configuration, since the setting values of the particle analyzer 2 are stored in the data fields 35g and 36b of database DB1 and database DB2, and the input table names specifying the storage region of the setting values and input item names are stored in the input table field 38c and input item field 38d of the database DB4, the input table names storing the desired setting values and input item names can be acquired from the database DB4, and the desired setting values can be read by accessing the region specified by the input table name and input item name. Furthermore, since the object name and the property name of the setting object is stored in the object field 38e and property field 38f of the database DB4, the object name and property name can be acquired from the database DB4, and the setting value can be set in the property specified by the property name of the object specified by the object name. Moreover, when, for example, a setting item is added and a setting vale is changed, only the necessary data in the databases DB1-DB4 need be revised without updating the application program 34a, thereby avoiding complex labor.

The components of the setting functions of the measuring apparatus of the application program 34a may be used in different types of measuring apparatuses than blood analyzers, urine analyzers, stool analyzers, and particle analyzer 2, and the setting functions applied to the measuring apparatus can be easily realized by carefully preparing the databases DB1-DB4 matching the object measuring apparatus, and the number of designs and number of development processes of the setting functions of the measuring apparatus can be reduced compared to the conventional art.

Furthermore, since the property values associated with an object name and property name can be included in the measurement result transmission data from the particle analyzer 2 to the data processing apparatus 3, and since the object name and property name of the control program 29e can be stored in the object field 39e and property field 39f of the database DB5, the necessary values and objects and properties corresponding to those values recorded in the database DB6 and DB7 can be specified. In addition, since the setting status (setting values) of the particle analyzer 2 during measurement and the measurement results can be stored in the fields 310b, 310c, and 311b-311i of the database DB6 and database DB7, and since the output table name and output field name of the storage destination of the value associated with the object name and property name can be stored in the output table field 39c and output field 39d of the database DB5, the output table name and output field name of the stored object can be acquired from the database DB5, and the values included in the received measurement result transmission data can be stored in the regions specified by the output table name and output field name. Thus, when, for example, data are added to the measurement result data recorded in a database, and the database recording destination of the measurement result data is changed, only the required data need be revised in the databases DB5-DB7 without updating the application program 34a, thus avoiding complex labor.

The components of the measurement result management functions of the measuring apparatus of the application program 34a may be used in different types of measuring apparatuses than blood analyzers, urine analyzers, stool analyzers, and particle analyzer 2, and the measurement result management functions applied to the measuring apparatus can be easily realized by carefully preparing the databases DB5-DB7 matching the object measuring apparatus, and the number of designs and number of development processes of the measurement result management functions of the measuring apparatus can be reduced compared to the conventional art.

Although, in the present embodiment, the data processing apparatus 3 is separate from the particle analyzer 2, the particle analyzer 2 and the data processing apparatus 3 are connected so as to be mutually capable of data communication, the setting of the particle analyzer 2 is accomplished from the data processing apparatus 3, and the measurement results and measuring time setting conditions of the particle analyzer 2 are managed by the data processing apparatus 3, it is to be noted that the function of the data processing apparatus 3 may be provided in the particle analyzer 2, and the measurement result and measuring time setting conditions may be managed along with setting the measuring conditions by the particle analyzer 2.

Although, in the present embodiment, when the input table name stored in the input table field 38c of the database DB4 is "SOPCODEDEF," the reading object is the database DB2 rather than the database DB3, however, the present invention is not limited to this example inasmuch as the database DB2 also may be specified as the reading object by the input table name "SOPMDT."

Although, in the present invention, the setting values stored in the RAM 31c are read rather than the setting values stored in the database DB2 on the hard disk 31d, and these setting values are sent to the particle analyzer 2 to set the particle analyzer 2, the present invention is not limited to this example inasmuch as when the setting values are transmitted the setting values may be red from the database DB2 on the hard disk 31d and these setting values may be sent to the particle analyzer 2.

Although the present embodiment has been described in terms of using the particle analyzer 2 as a measuring apparatus, the present invention is not limited to this example inasmuch as the invention also may be configured to set and manage measurement results of another measuring apparatus, such as, for example, hemocyte analyzer, blood coagulation analyzer, immunoanalyzer, urine material analyzer, urine qualitative analyzer, stool analyzer and the like.

Although the particle analyzer 2 and data processing apparatus 3 are separate in the present embodiment, the present invention is not limited to this example inasmuch as the functions of the data processing apparatus 3 may be added to the particle analyzer 2, such that the particle analyzer 2 and the data processing apparatus 3 are configured as a single integrated apparatus. Furthermore, the present invention is not limited to providing the databases DB1-DB7 on the hard disk 31*d* of the data processing apparatus 3 inasmuch as one or more of the databases DB1-DB7 may be provided on a data server separate from the data processing apparatus 3, such that the data processing apparatus 3 accesses the data server when reading or writing data to the databases DB1-DB7.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A method for setting operating condition of a measuring apparatus comprising the steps of:
   acquiring mutually associated storage region designation data and setting object designation data from a database storing mutually associated the storage region designation data and the setting object designation data, the storage region designation data designating the storage region for storing setting values used in setting the measuring apparatus, and the setting object designation data designating a setting object of the measuring apparatus;
   acquiring setting values from the storage region designated by the acquired storage region designation data; and
   setting the setting object designated by the acquired setting object designation data by the acquired setting value.

2. A measuring system comprising:
   a measuring apparatus provided with a plurality of setting objects;
   a data processing apparatus comprising a memory in which there are storable a first database for storing setting values used in setting the measuring apparatus and
   a second database for mutually associating and storing storage region designation data and setting object designation data, the storage region designation data designating a storage region at which the setting value is stored in the first database, and the setting object designation data designating the setting objects of the measuring apparatus,
   the data processing apparatus further comprising a first acquiring means functionality for acquiring the mutually associated storage region designation data and setting object designation data from the second database and
   a second acquiring functionality for acquiring the setting value from the storage region of the first database designated by the storage region designation data acquired by the first acquiring functionality; and
   the measuring system further comprising a setting functionality for setting the setting object designated by the setting object designation data acquired by the first acquiring by the setting value acquired by the second acquiring functionality.

3. The measuring system according to claim 2, wherein
   the second database stores mutually associated plurality of the storage region designation data, and plurality of the setting object designation data;
   the first acquiring functionality is configured so as to acquire the mutually associated storage region designation data and setting object designation data in a predetermined order from the second database; and
   the second acquiring functionality is configured so as to acquire the setting value from the storage region of the first database designated by the storage region designation data in accordance with the sequence in which the first acquiring functionality acquired the storage region designation data.

4. The measuring system according to claim 3, wherein
   the measuring apparatus comprises a control program having a plurality of objects; and
   the setting object comprises the object included in the control program of the measuring apparatus, and the properties of the object.

5. The measuring system according to claim 2, wherein the data processing apparatus further comprises a communication device for transmitting the setting object designation data acquired by the first acquiring functionality, and setting values acquired by the second acquiring functionality,
   the communication device is further configured to receive the setting object designation data and setting value transmitted from the data processing apparatus, and the measuring apparatus comprises the setting means.

6. The measuring system according to claim 5, wherein
   the data processing apparatus further comprises:
   a processor that executes computer programs; and
   a storage medium for storing a computer program to be executed by the processor;
   wherein the data processing apparatus is configured so as to function as the first acquiring functionality and second acquiring functionality when the processor executes the computer programs.

7. The measuring system according to claim 2, wherein
   the measuring apparatus is one among a blood analyzer, a urine analyzer, a stool analyzer, and a particle analyzer.

8. The measuring system according to claim 2, wherein
   the first acquiring functionality comprises:
   a third acquiring functionality for acquiring the storage region designation data from the second database; and
   a fourth acquiring functionality for acquiring the setting object designation data corresponding to the storage region designation data acquired by the third acquiring functionality from the second database.

9. A data processing apparatus that communicates with a measuring apparatus having a plurality of setting objects, comprising a memory in which there are storable
   a first database for storing setting values used for setting the measuring apparatus, and
   a second database for mutually associating and storing storage region designation data and setting object designation data, the storage region designation data designating a storage region at which the setting value is stored in the first database, and the setting object designation data designating the setting objects of the measuring apparatus;
   the data processing apparatus further comprising a first acquiring means functionality for acquiring the mutually associated storage region designation data and setting object designation data from the second database, a second acquiring functionality for acquiring the setting value from the storage region of the first database designated by the storage region designation data acquired by the first acquiring functionality, and a transmitter for transmitting the setting object designation data acquired by the first acquiring functionality, and the setting value acquired by the second acquiring functionality to the measuring apparatus.

10. The data processing apparatus according to claim 9, wherein the second database mutually associates and stores a plurality of the storage region designation data and plurality of the setting object designation data;

the first acquiring functionality is configured so as to acquire the mutually associated storage region designation data and setting object designation data in a predetermined order from the second database; and the second acquiring functionality is configured so as to acquire the setting value from the storage region of the first database designated by the storage region designation data in accordance with the sequence in which the first acquiring functionality acquired the storage region designation data.

11. The data processing apparatus according to claim 9, wherein the measuring apparatus comprises a control program having a plurality of objects; and the setting object comprises the object included in the control program of the measuring apparatus, and the properties of the object.

12. The data processing apparatus according to claim 9 further comprising:

a processor that executes computer programs; and a storage medium for storing computer programs to be executed by the processor;

wherein the data processing apparatus is configured so as to function as the first acquiring functionality and second acquiring functionality when the processor executes the computer programs.

13. The data processing apparatus according to claim 9, wherein the measuring apparatus is one among a blood analyzer, a urine analyzer, a stool analyzer, and a particle analyzer.

14. A computer readable storage medium storing a computer program that causes a computer which executes the computer program to function as:

a first acquiring functionality for acquiring storage region specification data and setting object specification data from a second database, wherein a first database stores setting values used for setting of operating condition of a measuring apparatus, and the second database stores storage region specification data specifying the storage region storing the setting value in the first database and setting object specification data specifying the setting objects of the measuring apparatus;

a second acquiring functionality for acquiring a setting value from the storage region of the first database specified by the storage region specification data acquired by the first acquiring means; and a transmitter for transmitting to the measuring apparatus the setting object specification data acquired by the first acquiring functionality and the setting values acquired by the second acquiring functionality.

* * * * *